(12) United States Patent
Poutiatine et al.

(10) Patent No.: US 8,574,189 B2
(45) Date of Patent: Nov. 5, 2013

(54) STORAGE AND DISPENSING DEVICES FOR ADMINISTRATION OF ORAL TRANSMUCOSAL DOSAGE FORMS

(75) Inventors: Andrew Poutiatine, Mill Valley, CA (US); Bruce Edwards, Menlo Park, CA (US); Charles Rampersaud, Castro Valley, CA (US); Pamela Palmer, San Francisco, CA (US); Bradley Blackwood, San Jose, CA (US); Benjamin K. Yaffe, San Francisco, CA (US)

(73) Assignee: AcelRx Pharmaceuticals, Inc., Redwood City, CA (US)

( * ) Notice: Subject to any disclaimer, the term of this patent is extended or adjusted under 35 U.S.C. 154(b) by 0 days.

(21) Appl. No.: 13/416,236

(22) Filed: Mar. 9, 2012

(65) Prior Publication Data

US 2012/0232473 A1 Sep. 13, 2012

Related U.S. Application Data

(63) Continuation of application No. 12/724,634, filed on Mar. 16, 2010, now Pat. No. 8,548,623.

(60) Provisional application No. 61/161,267, filed on Mar. 18, 2009.

(51) Int. Cl.
*A61M 31/00* (2006.01)
*A61F 13/20* (2006.01)

(52) U.S. Cl.
USPC .................... 604/59; 604/14; 604/15; 604/57

(58) Field of Classification Search
USPC ................................. 604/11, 14, 15, 57, 59
See application file for complete search history.

(56) References Cited

U.S. PATENT DOCUMENTS

| | | | |
|---|---|---|---|
| 2,621,655 A | 12/1952 | Olson et al. | |
| 3,162,322 A | 12/1964 | Gilbertson | |
| 3,444,858 A | 5/1969 | Russell | |
| 3,757,781 A * | 9/1973 | Smart | 604/59 |
| 3,780,735 A * | 12/1973 | Crouter et al. | 604/59 |
| 3,789,845 A * | 2/1974 | Long | 604/514 |
| 4,020,558 A | 5/1977 | Cournut et al. | |
| 4,060,083 A * | 11/1977 | Hanson | 604/59 |
| 4,237,884 A | 12/1980 | Erickson | |
| 4,474,308 A * | 10/1984 | Bergeron | 221/24 |
| 4,582,835 A | 4/1986 | Lewis et al. | |

(Continued)

FOREIGN PATENT DOCUMENTS

| | | |
|---|---|---|
| EP | 2114383 | 7/2010 |
| GB | 2309966 | 8/1997 |

(Continued)

OTHER PUBLICATIONS

ACTIQ® Fact Sheet (Mar. 2004).
Camu, F. et al., "Postoperative analgesic effects of three demand-dose sizes of fentanyl administered by patient-controlled analgesia," Anesth. Analg., 87:890-895 (1998).

(Continued)

*Primary Examiner* — Victoria P Shumate

(57) ABSTRACT

Dispensing devices and systems for oral transmucosal administration of small volume drug dosage forms to the oral mucosa are provided. The dispensing device may be a single dose applicator (SDA), or an electromechanical device comprising a means for patient identification such as a wrist worn RFID tag and annular bidirectional antenna together with a lock-out feature.

24 Claims, 10 Drawing Sheets

(56) References Cited

U.S. PATENT DOCUMENTS

| | | |
|---|---|---|
| 4,764,378 A | 8/1988 | Keith et al. |
| 4,785,969 A | 11/1988 | McLaughlin |
| 4,950,234 A | 8/1990 | Fujioka et al. |
| 5,190,185 A | 3/1993 | Blechl |
| 5,263,596 A | 11/1993 | Williams |
| 5,292,307 A * | 3/1994 | Dolzine et al. ............... 604/514 |
| 5,296,234 A | 3/1994 | Hadaway et al. |
| 5,348,158 A | 9/1994 | Honan et al. |
| 5,489,025 A | 2/1996 | Romick |
| 5,507,277 A | 4/1996 | Rubsamen et al. |
| 5,507,807 A | 4/1996 | Shippert |
| 5,549,560 A * | 8/1996 | Van de Wijdeven .......... 604/130 |
| 5,584,805 A * | 12/1996 | Sutton ............................ 604/60 |
| 5,657,748 A | 8/1997 | Braithwaite |
| 5,660,273 A | 8/1997 | Discko, Jr. |
| 5,694,919 A | 12/1997 | Rubsamen et al. |
| 5,710,551 A | 1/1998 | Ridgeway |
| 5,724,957 A | 3/1998 | Rubsamen et al. |
| 5,752,620 A | 5/1998 | Pearson |
| 5,850,937 A | 12/1998 | Rauche |
| 5,860,946 A * | 1/1999 | Hofstatter ....................... 604/15 |
| 5,945,651 A | 8/1999 | Chorosinski et al. |
| 5,950,632 A | 9/1999 | Reber et al. |
| 5,954,641 A | 9/1999 | Kehr et al. |
| 5,968,547 A | 10/1999 | Reder et al. |
| 5,984,888 A * | 11/1999 | Nielsen et al. .................. 604/12 |
| 5,995,938 A | 11/1999 | Whaley |
| 5,997,518 A | 12/1999 | Laibovitz et al. |
| 6,039,251 A | 3/2000 | Holowko et al. |
| 6,116,414 A | 9/2000 | Discko, Jr. |
| 6,131,765 A | 10/2000 | Barry et al. |
| 6,171,294 B1 | 1/2001 | Southam et al. |
| 6,190,326 B1 | 2/2001 | McKinnon et al. |
| 6,216,033 B1 | 4/2001 | Southam et al. |
| 6,230,927 B1 | 5/2001 | Schoonen et al. |
| 6,234,343 B1 | 5/2001 | Papp |
| 6,294,999 B1 | 9/2001 | Yarin et al. |
| 6,310,072 B1 | 10/2001 | Smith et al. |
| 6,319,510 B1 | 11/2001 | Yates |
| 6,328,159 B1 | 12/2001 | Discko, Jr. |
| 6,364,158 B1 | 4/2002 | Dimoulis |
| 6,425,495 B1 | 7/2002 | Senda et al. |
| 6,484,718 B1 | 11/2002 | Schaeffer |
| 6,495,120 B2 | 12/2002 | McCoy et al. |
| 6,541,021 B1 | 4/2003 | Johnson et al. |
| 6,564,967 B1 | 5/2003 | Stringfield et al. |
| 6,605,060 B1 | 8/2003 | O'Neil |
| 6,651,651 B1 | 11/2003 | Bonney et al. |
| 6,660,295 B2 | 12/2003 | Watanabe et al. |
| 6,682,716 B2 | 1/2004 | Hodges et al. |
| 6,726,053 B1 | 4/2004 | Harrold |
| 6,752,145 B1 | 6/2004 | Bonney et al. |
| 6,762,684 B1 | 7/2004 | Camhi et al. |
| 6,776,978 B2 | 8/2004 | Rabinowitz et al. |
| 6,793,075 B1 | 9/2004 | Jeter |
| 6,796,429 B2 | 9/2004 | Cameron et al. |
| 6,824,512 B2 | 11/2004 | Warkentin et al. |
| 6,835,194 B2 | 12/2004 | Johnson et al. |
| 6,855,310 B2 | 2/2005 | Rabinowitz et al. |
| 6,881,208 B1 | 4/2005 | Phipps et al. |
| 6,914,668 B2 | 7/2005 | Brestel et al. |
| 6,959,808 B2 | 11/2005 | Discko, Jr. |
| 7,004,111 B2 | 2/2006 | Olson et al. |
| 7,018,619 B2 | 3/2006 | Rabinowitz et al. |
| 7,044,125 B2 | 5/2006 | Vedrine et al. |
| 7,070,762 B2 | 7/2006 | Rabinowitz et al. |
| 7,070,764 B2 | 7/2006 | Rabinowitz et al. |
| 7,072,738 B2 | 7/2006 | Bonney et al. |
| 7,078,019 B2 | 7/2006 | Rabinowitz et al. |
| 7,090,830 B2 | 8/2006 | Hale |
| 7,118,550 B2 | 10/2006 | Loomis |
| 7,172,573 B1 * | 2/2007 | Lamb ............................ 604/59 |
| 7,264,139 B2 | 9/2007 | Brickwood et al. |
| 7,458,374 B2 | 12/2008 | Hale et al. |
| 7,468,179 B2 | 12/2008 | Rabinowitz et al. |
| 7,484,642 B2 | 2/2009 | Bonney et al. |
| 7,500,444 B2 | 3/2009 | Bonney et al. |
| 7,540,998 B2 * | 6/2009 | Terwilliger et al. ............. 422/28 |
| 7,552,728 B2 | 6/2009 | Bonney et al. |
| 7,581,657 B2 | 9/2009 | Dickmann |
| 7,744,558 B2 * | 6/2010 | Maag .............................. 604/57 |
| 8,062,248 B2 | 11/2011 | Kindel |
| 8,142,733 B2 | 3/2012 | Creaven |
| 2001/0020147 A1 | 9/2001 | Staniforth et al. |
| 2003/0015197 A1 | 1/2003 | Hale et al. |
| 2003/0017175 A1 | 1/2003 | Cutler |
| 2003/0022910 A1 | 1/2003 | Cutler |
| 2003/0052135 A1 | 3/2003 | Conley et al. |
| 2003/0052787 A1 | 3/2003 | Zerhusen et al. |
| 2003/0077300 A1 | 4/2003 | Wermeling et al. |
| 2003/0099158 A1 | 5/2003 | De La Huerga |
| 2003/0132239 A1 | 7/2003 | Konig et al. |
| 2003/0173408 A1 | 9/2003 | Mosher et al. |
| 2003/0185872 A1 | 10/2003 | Kochinke |
| 2003/0190290 A1 | 10/2003 | Ross |
| 2004/0025871 A1 | 2/2004 | Davies |
| 2004/0094564 A1 | 5/2004 | Papp |
| 2004/0133305 A1 | 7/2004 | Jean-Pierre |
| 2004/0158349 A1 | 8/2004 | Bonney et al. |
| 2004/0180080 A1 | 9/2004 | Furusawa et al. |
| 2004/0253307 A1 | 12/2004 | Hague et al. |
| 2005/0049464 A1 | 3/2005 | Lassers et al. |
| 2005/0089479 A1 | 4/2005 | Rabinowitz et al. |
| 2005/0101936 A1 | 5/2005 | Gonzales et al. |
| 2005/0122219 A1 | 6/2005 | Petersen et al. |
| 2005/0131386 A1 * | 6/2005 | Freeman et al. .............. 604/522 |
| 2005/0150488 A1 | 7/2005 | Dave |
| 2005/0150489 A1 | 7/2005 | Dunfield et al. |
| 2005/0258066 A1 | 11/2005 | Conley |
| 2006/0031099 A1 | 2/2006 | Vitello et al. |
| 2006/0089858 A1 | 4/2006 | Ling |
| 2006/0229570 A1 | 10/2006 | Lovell et al. |
| 2007/0074722 A1 | 4/2007 | Giroux et al. |
| 2007/0186923 A1 | 8/2007 | Poutiatine et al. |
| 2007/0207207 A1 | 9/2007 | Tzannis et al. |
| 2007/0260491 A1 | 11/2007 | Palmer et al. |
| 2007/0286900 A1 | 12/2007 | Herry et al. |
| 2007/0299687 A1 | 12/2007 | Palmer et al. |
| 2008/0147044 A1 | 6/2008 | Palmer et al. |
| 2008/0164275 A1 | 7/2008 | Poutiatine et al. |
| 2008/0166404 A1 | 7/2008 | Tzannis et al. |
| 2008/0203107 A1 | 8/2008 | Conley et al. |
| 2008/0268023 A1 | 10/2008 | Palmer et al. |
| 2009/0010992 A1 | 1/2009 | Palmer et al. |
| 2009/0048237 A1 | 2/2009 | Palmer et al. |
| 2009/0131479 A1 | 5/2009 | Palmer et al. |
| 2010/0105735 A1 | 4/2010 | Palmer et al. |
| 2010/0130551 A1 | 5/2010 | Pushpala et al. |
| 2010/0137836 A1 | 6/2010 | Palmer et al. |
| 2010/0253476 A1 | 10/2010 | Poutiatine et al. |
| 2010/0256190 A1 | 10/2010 | Palmer et al. |
| 2011/0091544 A1 | 4/2011 | Palmer |
| 2011/0208118 A1 * | 8/2011 | Katz ............................... 604/57 |
| 2011/0288128 A1 | 11/2011 | Palmer et al. |
| 2012/0035216 A1 | 2/2012 | Palmer et al. |
| 2013/0090594 A1 | 4/2013 | Palmer et al. |
| 2013/0131586 A1 | 5/2013 | Poutiatine et al. |

FOREIGN PATENT DOCUMENTS

| | | |
|---|---|---|
| JP | 2000-142841 | 5/2000 |
| JP | 2003-525081 | 8/2003 |
| JP | 2007-517636 | 7/2007 |
| WO | WO 02/32487 | 4/2002 |
| WO | WO 02/074372 | 9/2002 |
| WO | WO 02/078594 | 10/2002 |
| WO | WO 03/092575 | 11/2003 |
| WO | WO 2004/067004 | 8/2004 |
| WO | WO 2004/080515 | 9/2004 |

OTHER PUBLICATIONS

Chelly, J. E. et al., "The safety and efficacy of a fentanyl patient-controlled transdermal system for acute postoperative analgesia: a

(56) References Cited

OTHER PUBLICATIONS multicenter, placebo-controlled trial," Anesth. Analg., 98:427-433 (2004).
Culling et al., "Haemodynamics and plasma concentrations following sublingual GTN and intravenous, or inhaled isosorbide dinitrate," Br. J. Clin. Pharm., 17:125-131 (1984).
Drug Information Bulletin [online], 37(4) (Sep./Oct. 2004), [Retrieved on Jun. 5, 2008.] Retrieved from the Internet: <URL: http://www.kgh.on.ca/pharmacy/diBulletinSeptOct2004.pdf>, 4 pages.
FDA Guidance for Industry: Container Closure Systems for Packaging Human Drugs and Biologics, pp. 1-E2 (1999).
Fentora™ Package Insert (2006).
Fentora®, 2008 Red Book, p. 174.
Griffin, D. et al., Reg. Anesth. Pain Med., vol. 10, American Society of Regional Anesthesia Spring Meeting (2010).
Infusion Pump Improvement Initiative, Center for Devices and Radiological Health, U.S. Food and Drug Administration, Apr. 2010, 7 pages.
Rawal, N. et al., "Current practices for postoperative pain management in Europe and the potential role of the fentanyl HCl iontophoretic transdermal system," European Journal of Anaesthesiology, 24:299-308 (2007).
Rosati, J. et al., "Evaluation of an oral patient-controlled analgesia device for pain management in oncology inpatients," J. Support. Oncol., 5(9):443-448 (2007).
Rothschild, J. M. et al., "A controlled trial of smart infusion pumps to improve medication safety in critically ill patients," Crit. Care Med., 33(3):533-540 (2005).
Shojaei, A. H. et al., "*Buccal mucosa* as a route for systemic drug delivery: a review," Journal of Pharmacy and Pharmaceutical Sciences, 1:15-30 (1998).
Slatkin et al., "Fentanyl Buccal Tablet for Relief of Breakthrough Pain in Opioid-Tolerant Patients With Cancer-Related Chronic Pain," J. of Supportive Oncol., vol. 5, No. 7, Jul./Aug. 2007, pp. 327-334.
Sufenta® Package Insert (2006), 3 pages.
Vadivelu, N. et al., "Recent advances in postoperative pain management," Yale Journal of Biology and Medicine, 83:11-25 (2010).
Van Raders, P. et al., "Nurses' views on ease of patient care in postoperative pain management," British Journal of Nursing, 16(5):312-317 (2007).
Vasight, N. et al., "Formulation selection and pharmacokinetic comparison of fentanyl buccal soluble film with oral transmucosal fentanyl citrate," Clin. Drug Investig., 29(10):647-654 (2009).
Vercauteren, M. P. et al., "Epidural sufentanil for postoperative patient-controlled analgesia (PCA) with or without background infusion: a double-blind comparison," Anesth. Analg., 80:76-80 (1995).
Viscusi, E. R., "Patient-controlled drug delivery for acute postoperative pain management: a review of current and emerging technologies," Regional Anesthesia and Pain Medicine, 33(2):146-158 (2008).
Abrams, R. et al., "Safety and Effectiveness of Intranasal Administration of Sedative Medications (Ketamine, Midazolam, or Sufentanil) for Urgent Brief Pediatric Dental Procedures," Anesth Prog., 40:63-66 (1993).
AcelRx Pharmaceuticals, "AcelRx Pharmaceuticals Reports Positive Results from a Clinical Trial of Sublingual Sufentanil/Triazolam NanoTabTM Combination (ARX-03) in Treating Procedural Pain and Anxiety," Jan. 12, 2009, pp. 1-2.
Ahmad, S. et al., "Fentanyl HCl iontophoretic transdermal system versus intravenous morphine pump after gynecologic surgery," Arch Gynecol Obstet 276:251-258 (2007).
Albert, J. M. et al., "Patient-Controlled Analgesia vs. Conventional Intramuscular Analgesia Following Colon Surgery," Diseases of the Colon & Rectum, 31(2):84-86 (1988).
Bredenberg, S., "New Concepts in Administration of Drugs in Tablet Form—Formulations and Evaluation of a Sublingual Tablet for Rapid Absorption, and Presentation of an Individualised Dose Administration System," Comprehensive Summaries of Uppsala Dissertations from the Faculty of Pharmacy 287, ACTA Universitatis Upsaliensis Uppsala (2003).
Bredenberg, S. et al., "In Vitro and in Vivo Evaluation of a New Sublingual Tablet System for Rapid Oromucosal Absorption Using Fentanyl Citrate as the Active Substance," European Journal of Pharmaceutical Sciences, 20:327-334 (2003).
Christie, JM, et al., "Dose-titration, multi-center study of oral transmucosal fentanyl citrate for the treatment of breakthrough pain in cancer patients using transdermal fentanyl for persistent pain," J Clin Oncol. 16(10):3238-45 (1998).
Coda, BA, et al., "Comparative efficacy of patient-controlled administration of morphine, hydromorphone, or sufentanil for the treatment of oral mucositis pain following bone marrow transplantation," Pain, 72:333-346 (1997).
Collins, LMC, Dawes C, "The Surface Area of the Adult Human Mouth and Thickness of the Salivary Film Covering the Teeth and Oral Mucosa," J Dent Res, 66(8):1300-2 (1987).
Dale, O. et al., "Nasal Administration of Opioids for Pain Management in Adults," Acta Anaesthesiol. Scand., 46:759-770 (2002).
Darwish, M. et al., "Single-Dose and Steady-State Pharmacokinetics of Fentanyl Buccal Tablet in Healthy Volunteers," Journal of Clinical Pharmacology, 47:56-63 (2007).
Darwish, M. et al., "Pharmacokinetics and Dose Proportionality of Fentanyl Effervescent Buccal Tablets in Healthy Volunteers," Clinical Pharmacokinetics, 44(12): 1279-1286 (2005).
Darwish, M. et al., "Comparison of Equivalent Doses of Fentanyl Buccal Tablets and Arteriovenous Differences in Fentanyl Pharmacokinetics," Clinical Pharmacokinetics, 45(8):843-850 (2006).
Darwish, M. et al., "Pharmacokinetic Properties of Fentanyl Effervescent Buccal Tablets: A Phase I, Open-Label, Crossover Study of Single-Dose 100, 200, 400, and 800 µg in Healthy Adult Volunteers," Clinical Therapeutics, 28(5):707-714 (2006).
Darwish, M. et al., "Relative Bioavailability of the Fentanyl Effervescent Buccal Tablet (FEBT) 1080 µg Versus Oral Transmucosal Fentanyl Citrate 1600 µg and Dose Proportionality of FEBT 270 to 1300 µg: A Single-Dose, Randomized, Open-Label, Three-Period Study in Healthy Adult Volunteers," Clinical Therapeutics, 28(5):715-724 (2006).
Darwish, M. et al., "Effect of Buccal Dwell Time on the Pharmacokinetic Profile of Fentanyl Buccal Tablet," Expert Opin. Pharmacother., 8(13):2011-2016 (2007).
Darwish, M. et al., "Bioequivalence Following Buccal and Sublingual Placement of Fentanyl Buccal Tablet 400 µg in Healthy Subjects," Clin. Drug Invest., 28(1):1-7 (2008).
Darwish, M. et al., Absolute and Relative Bioavailability of Fentanyl Buccal Tablet and Oral Transmucosal Fentanyl Citrate, Journal of Clinical Pharmacology, 47:343-350 (2007).
deVries, M. et al., "Developments in Buccal Drug Delivery," Critical Reviews in Therapeutic Drug Carrier Systems, 8(3):271-303 (1991).
Enting, R.H. et al., "The 'Pain Pen' for Breakthrough Cancer Pain: A Promising Treatment," Journal of Pain and Symptom Management, 29(2):213-217 (2005).
Fisher, DM, et al., "Pharmacokinetics of an Implanted Osmotic Pump Delivering Sufentanil for the Treatment of Chronic Pain," Anesthesiology, 99(4):929-37 (Oct. 2003).
Gardner-Nix, J., "Oral Transmucosal Fentanyl and Sufentanil for Incident Pain," Journal of Pain and Symptom Management, 22(2):627-630 (Aug. 2001).
Grass, J., "Patient-Controlled Analgesia," Anesth. Analg., 101:S44-S61 (2005).
Hicks, R. et al., "USP Medication Safety Forum: Medication Errors Involving Patient-Controlled Analgesia," Joint Commission on Quality and Patient Safety, 34(12):734-742 (2008).
KGH Drug Information Bulletin, "Sublingual Sufentanil for Incident Pain," KGH Drug Information Bulletin, 37(4):2 (2004).
Kunz, K. M., et al., "Severe Episodic Pain: Management with Sublingual Sufentanil," Journal of Pain and Symptom Management, 8(4):189-190 (1993).
Mathieu, N. et al., "Intranasal Sufentanil is Effective for Postoperative Analgesia in Adults," Canadian Journal of Anesthesia, 53(1):60-66 (2006).

(56) References Cited

OTHER PUBLICATIONS

Reisfield, G. et al., "Rational Use of Sublingual Opioids in Palliative Medicine," Journal of Palliative Medicine, 10(2):465-475 (2007).
Striebel HW, et al., "Patient-controlled intranasal analgesia (PCINA) for the management of postoperative pain: a pilot study," J Clin Anesth, 8:4-8 (Feb. 1996).
Striebel HW, et al., "Patient-controlled intranasal analgesia: a method for noninvasive postoperative pain management," Anesth Analg, 83:548-51 (1996).
Viscusi E.R., et al., "An iontophoretic fentanyl patient-activated analgesic delivery system for postoperative pain: a double-blind, placebo-controlled trial," Anesth Analg. Jan. 2006;102(1):188-94.
Viscusi E.R., et al., "Patient-Controlled Transdermal Fentanyl Hydrochloride vs Intravenous Morphine Pump for Postoperative Pain: A randomized controlled trial," JAMA, 291(11):1333-1341 (2004).
Weinberg, D. S. et al., "Sublingual Absorption of Selected Opioid Analgesics," Clin. Pharmacol. Ther., 44(3):335-342 (Sep. 1988).
Zhang, H., et al., "Oral Mucosal Drug Delivery: Clinical Pharmacokinetics and Therapeutic Applications," Clinical Pharmacokinetics, 41(9):661-680 (2002).
International Search Report and Written Opinion for International Application No. PCT/US2011/037401, mailed Aug. 19, 2011.
Office Action for U.S. Application No. 12/580,930, mailed Oct. 21, 2011.
International Search Report and Written Opinion for International Application No. PCT/US2010/027437, mailed Jun. 21, 2010.
Office Action for U.S. Appl. No. 12/275,485, mailed Mar. 2, 2011.
Office Action for U.S. Appl. No. 12/275,485, mailed Nov. 23, 2011.
Office Action U.S. Appl. No. 11/429,904, mailed Sep. 17, 2008.
Office Action U.S. Appl. No. 11/429,904, mailed Mar. 5, 2009.
Office Action U.S. Appl. No. 11/429,904, mailed Aug. 20, 2009.
Office Action U.S. Appl. No. 11/473,551, mailed Sep. 26, 2008.
Office Action U.S. Appl. No. 11/473,551, mailed Mar. 16, 2009.
Office Action U.S. Appl. No. 11/473,551, mailed Sep. 11, 2009.
Office Action for U.S. Appl. No. 11/825,251, mailed Aug. 5, 2010.
Supplementary European Search Report for European Application No. EP07716450, mailed Apr. 6, 2011.
Office Action for U.S. Appl. No. 11/650,230, mailed Sep. 25, 2008.
Office Action for U.S. Appl. No. 11/650,230, mailed Mar. 10, 2009.
Office Action for U.S. Appl. No. 11/650,230, mailed Aug. 4, 2009.
Office Action for U.S. Appl. No. 11/650,230, mailed Feb. 2, 2010.
Office Action for U.S. Appl. No. 11/650,230, mailed Jun. 16, 2010.
Office Action for U.S. Appl. No. 11/650,230, mailed Mar. 1, 2011.
International Search Report and Written Opinion for International Application No. PCT/US2007/000527, mailed Dec. 17, 2007.
International Preliminary Report on Patentability for International Application No. PCT/US2007/000527, dated Feb. 24, 2009.
Office Action for U.S. Appl. No. 11/825,212, mailed Mar. 24, 2010.
Office Action for U.S. Appl. No. 11/825,212, mailed Aug. 31, 2010.
International Search Report and Written Opinion for International Application No. PCT/US2007/089016, mailed Jun. 17, 2008.
International Preliminary Report on Patentability for International Application No. PCT/US2007/089016, dated Jul. 7, 2009.
Office Action for U.S. Appl. No. 11/980,216, mailed Dec. 24, 2008.
Office Action for U.S. Appl. No. 11/980,216, mailed Jul. 20, 2009.
Office Action for U.S. Appl. No. 11/980,216, mailed Jan. 5, 2010.
Office Action for U.S. Appl. No. 11/980,216, mailed Jul. 2, 2010.
International Search Report and Written Opinion for International Application No. PCT/US2007/089017, mailed Jun. 23, 2008.
International Preliminary Report on Patentability for International Application No. PCT/US2007/089017, dated Jul. 7, 2009.
Office Action for U.S. Appl. No. 11/985,162, mailed Dec. 20, 2010.
International Search Report and Written Opinion for International Application No. PCT/US2007/089018, mailed Oct. 15, 2008.
Office Action for U.S. Appl. No. 12/521,983, mailed Feb. 15, 2012.
Notice of Allowance for U.S. Appl. No. 12/724,634, mailed May 3, 2013.
Office Action for Canadian Application No. 2,636,115, dated Feb. 12, 2013.
Keohane, C. A. et al., "Intravenous medication safety and smart infusion systems," Journal of Infusion Nursing, 28(5):321-328 (Sep./Oct. 2005).
Kotey, G. A. et al., "Iontophoretic delivery of fentanyl for acute post-operative pain management," The European Journal of Hospital Pharmacy Science, 13(1):3-9 (2007).
Lin, L. et al., "Applying human factors to the design of medical equipment: patient-controlled analgesia," J. Clin. Monitoring and Computing, 14:253-263 (1998).
McInnes, F. et al., "Evaluation of the clearance of a sublingual buprenorphine spray in the beagle dog using gamma scintigraphy," Pharmaceutical Research, (2007), 6 pages.
Miaskowski, C., "Patient-controlled modalities for acute postoperative pain management," Journal of PeriAnesthesia Nursing, 20(4):255-267 (Aug. 2005).
Miller, R. D., "The pursuit of excellence. The 47th Annual Rovenstine Lecture," Anesthesiology, 110(4):714-720 (Apr. 2009).
Minkowitz et al., Reg. Anesth. Pain Med., vol. 8, American Society of Regional Anesthesia Spring Meeting (2010).
Momeni, M. et al., "Patient-controlled analgesia in the management of postoperative pain," Drugs, 66(18):2321-2337 (2006).
Onsolis Package Insert (Jul. 2009), 11 pages.
Rawal, N. et al., "Current practices for postoperative pain management in Europe and the potential role of the fentanyl HCl iontophoretic transdermal system," European Journal of Anaesthesiology, 24:299-308 (2007).
International Search Report and Written Opinion for International Application No. PCT/US2007/010822, mailed Aug. 5, 2008.
International Search Report and Written Opinion for International Application No. PCT/US2007/011337, mailed Aug. 21, 2008.
Office Action for U.S. Appl. No. 11/650,230, mailed Mar. 27, 2012.
Office Action for Japanese Patent Application No. 2009-544898, mailed Jul. 24, 2012.
Office Action for Japanese Application No. 2009-544899, mailed Aug. 1, 2012.

* cited by examiner

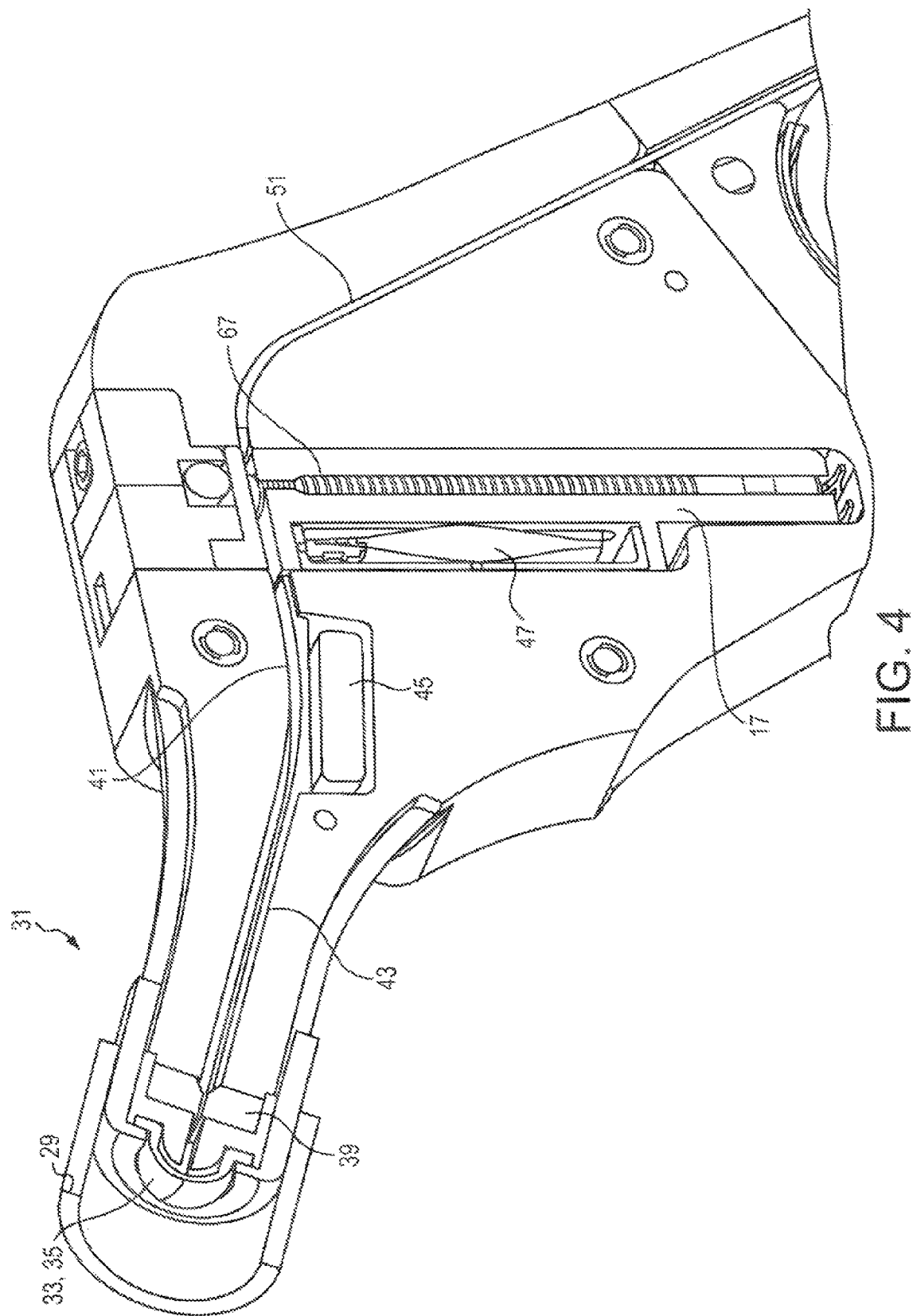

FIG. 6C
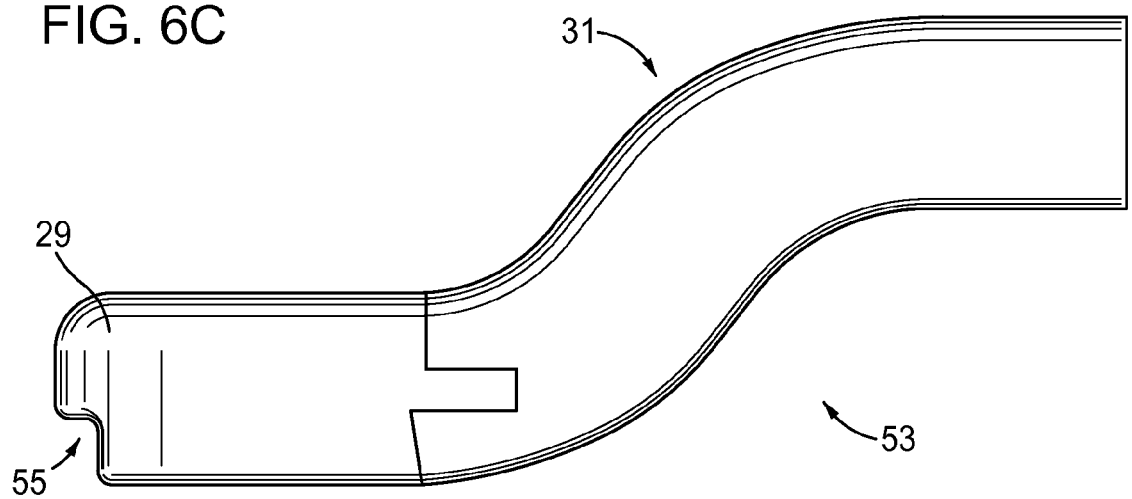
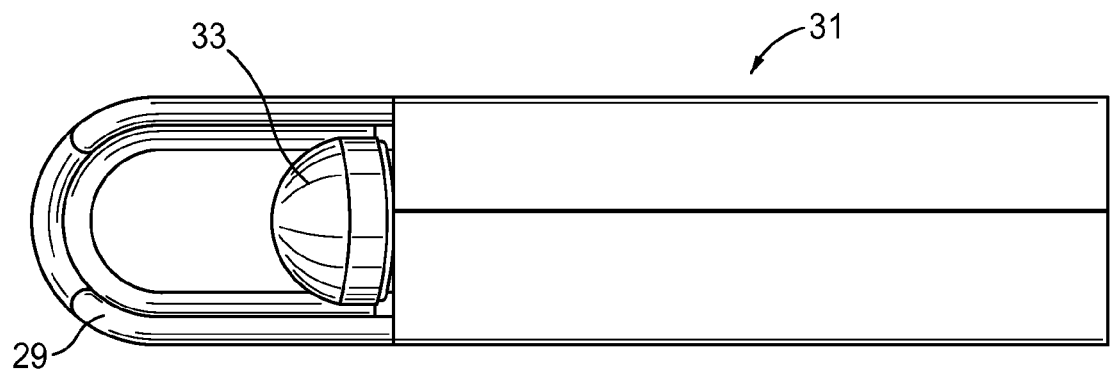
FIG. 6D

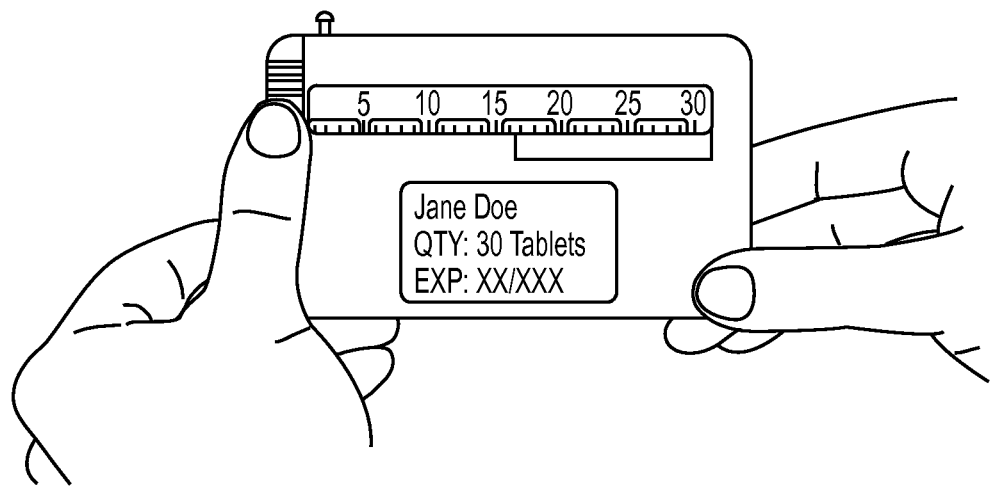
FIG. 8A
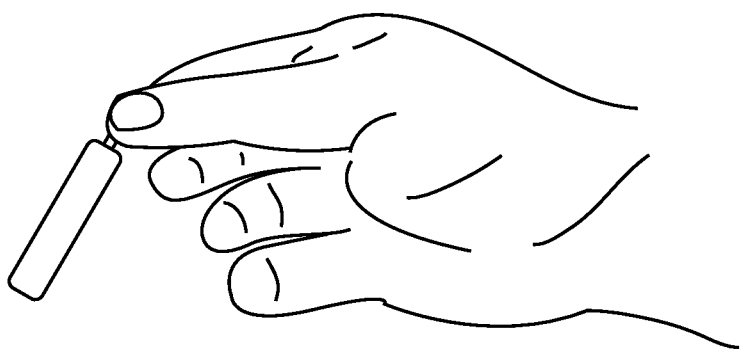
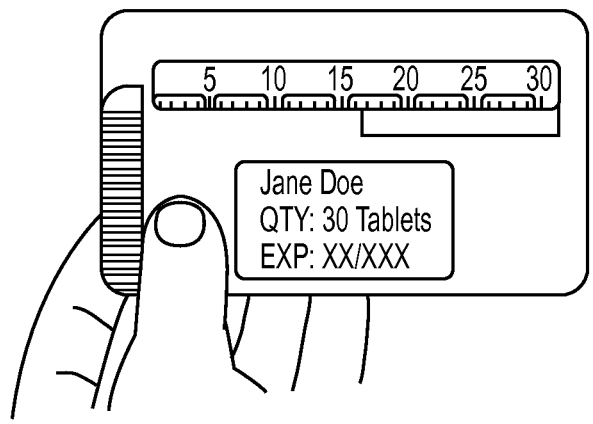
FIG. 8B

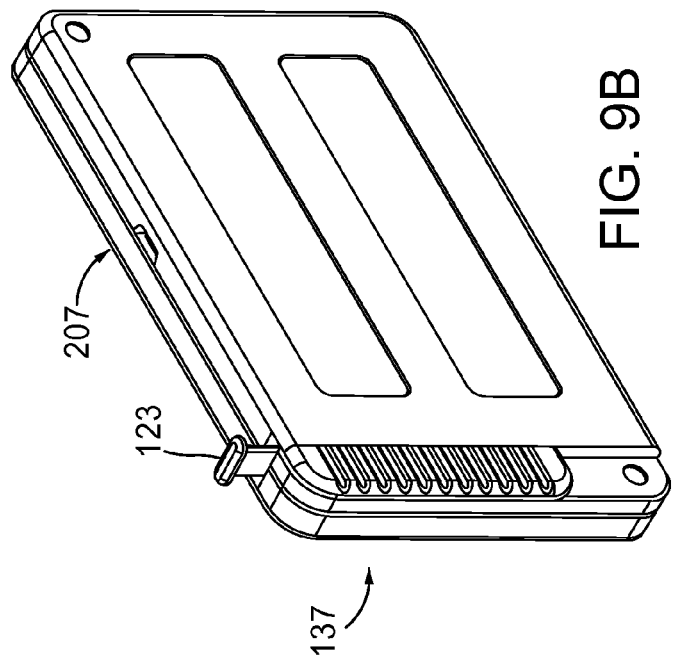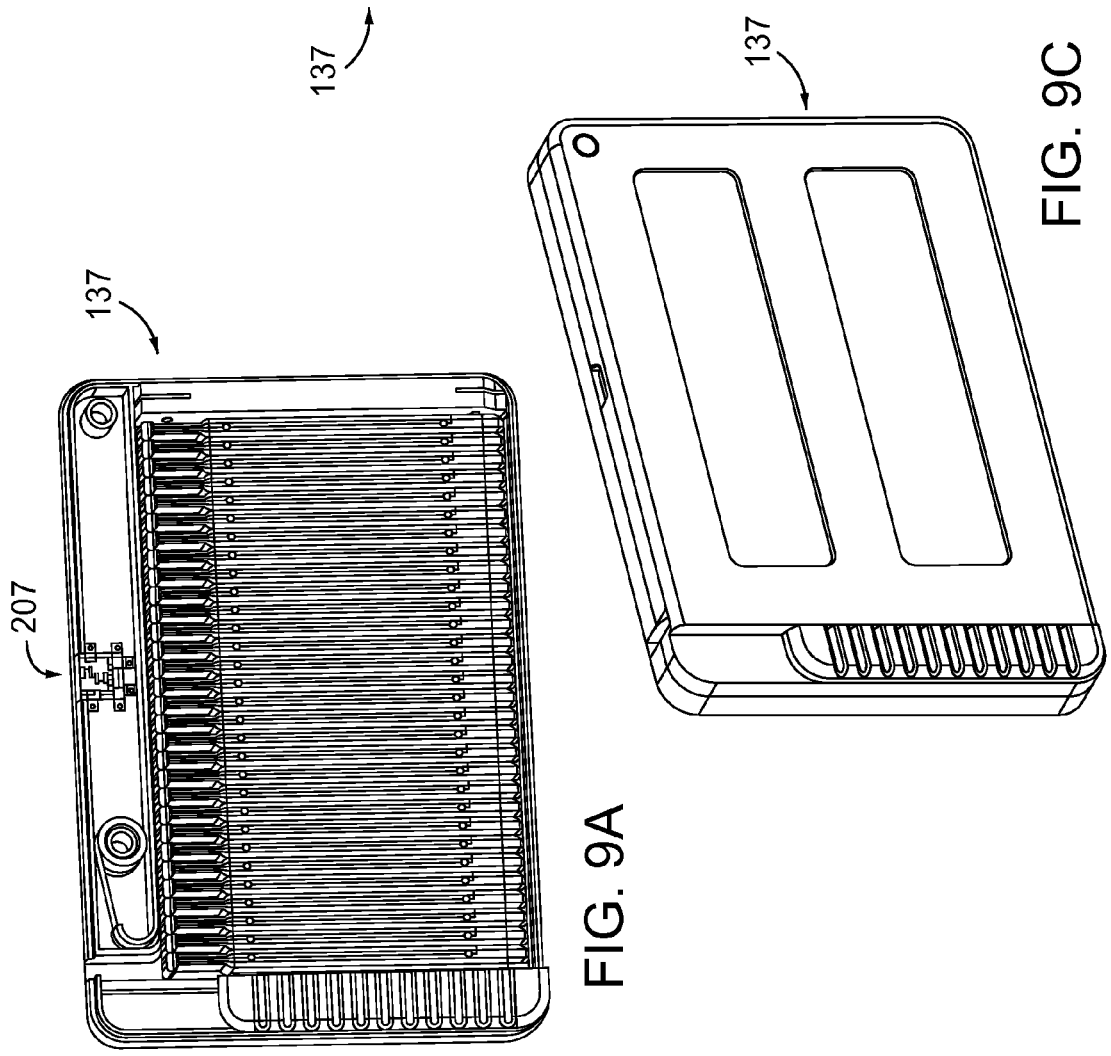

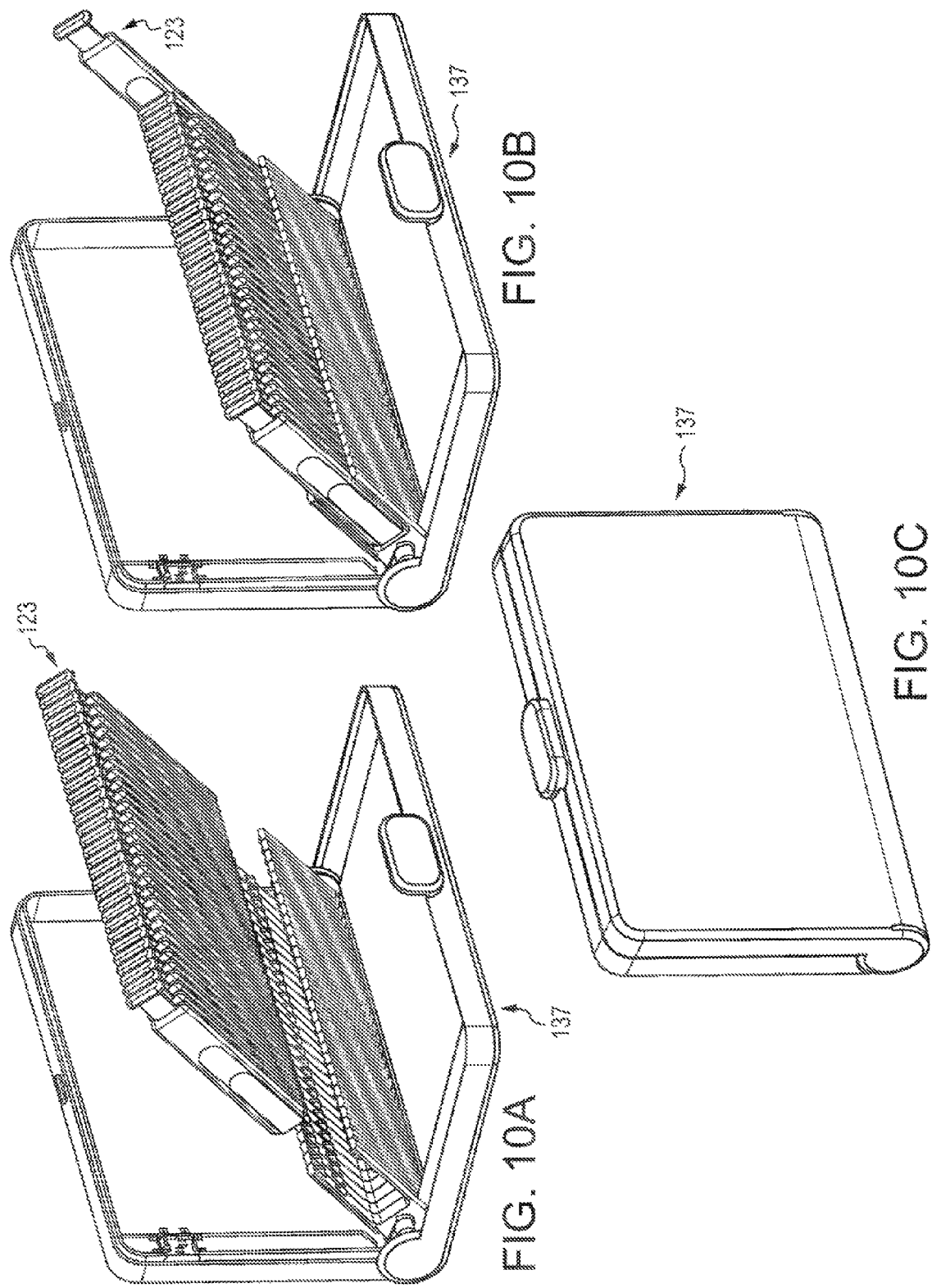

STORAGE AND DISPENSING DEVICES FOR ADMINISTRATION OF ORAL TRANSMUCOSAL DOSAGE FORMS

CROSS REFERENCE TO OTHER APPLICATIONS

This application is a continuation of and claims priority to U.S. application Ser. No. 12/724,634, filed Mar. 16, 2010, entitled, "Storage and Dispensing Devices for Administration of Oral Transmucosal Dosage Forms," which claims priority to and the benefit of U.S. Provisional Application Ser. No. 61/161,267, filed Mar. 18, 2009, entitled, "Storage and Dispensing Devices for Administration of Oral Transmucosal Dosage Forms," each of which is incorporated by reference herein in its entirety.

FIELD OF THE INVENTION

The present invention relates to dispensing devices and systems for oral transmucosal administration of small volume drug dosage forms (tablets) to the oral mucosa. The dispensing device may be a single dose applicator (SDA) or an electromechanical device comprising a wrist worn RFID tag and annular bidirectional antenna.

BACKGROUND OF THE TECHNOLOGY

Many medications that are dosed "as-needed" in a hospital or institutional setting require a restricted dosing schedule for safe self-administration.

Intravenous (IV) patient controlled analgesia (PCA) pumps are typically used to administer medications, such as opioids, for treatment of pain in the hospital or institutional setting, as well as on an outpatient basis. Using a preprogrammed PCA pump, the patient receives each dose of intravenous medication by activating a bedside button at allowable time intervals. If the button is activated during a time interval in which an allowable dose has already been administered, the pump is "locked out" and unable to deliver the dose until the appropriate time interval has passed. This prevents the patient from taking more than a maximum allowable dose of medication during a measured time interval.

There is a current focus on patient safety in medication administration, and the Institute for Safe Medication Practices (ISMP) and the Joint Commission on the Accreditation of Healthcare Organizations (JCAHO) have identified several consistently problematic areas in the use of IV PCA, the most problematic being human and pump errors, examples of which include pump programming errors based on entry of the wrong medication concentration; confusion over milligrams versus milliliters; the loading dose programmed as a bolus dose; the incorrect lockout time selected; and a PCA bolus dose confused with the basal rate. Also problematic is PCA by proxy, where the PCA button is activated by someone other than the patient, most commonly family members, nurses; or friends. See, e.g., Hicks, et al., Joint Commission on Quality and Patient Safety, 34(12), 734-742, 2008.

Oral mucosal drug delivery is an alternative method of systemic drug delivery that offers several advantages over both injectable, e.g., IV, and traditional oral routes of administration. The oral mucosa is highly vascularized, allowing lipophillic drugs to be readily absorbed through the oral mucosa and directly enter the systemic circulation, bypassing the gastrointestinal (GI) tract and first-pass metabolism in the liver.

Many medications have been evaluated for oral transmucosal delivery, however, few are commercially available. Further, although dispensing devices are available for the administration of a variety of types of medications, only inhaled medications are typically administered though the mouth using a device.

In addition, young children are vulnerable to inadvertent exposure to medications, in particular, when medications are not stored securely. Child-resistant packaging is required for many prescription medications as well as many household products. Child-resistant packaging together with "smart" packaging, has resulted in enhanced patient safety. "Smart" packaging or packaging-identification technology such as Radio Frequency Identification (RFID) tags provide a viable means of medical-packaging traceability. RFID technology can provide controlled access to medications and help ensure patient safety and compliance.

SUMMARY OF THE INVENTION

Controlled access medication dispensers are provided by the claimed invention.

A radio frequency identification (RFID) system for patient identification is provided. The system comprises a handheld device having an RFID reader antenna, and a matching wrist worn RFID tag or inlay consisting essentially of a die or chip, a circuit and an antenna, wherein the antenna comprises annular conductors that circumvent the wrist. The antenna field has an axis directed at the patient's hand, such that patient identification occurs when a handheld device comprising the reader antenna is held in the patient's hand, resulting in activation of the reader antenna.

The wrist worn RFID tag or inlay may be a bracelet and the RFID signal may be directional and symmetrical or bidirectional, but not symmetrical. In one embodiment, the distance between the handheld device and the wrist worn RFID tag or inlay is between 0 inches and 12 inches, between 0 and 8 inches, or between 0 and 6 inches.

Further provided is a drug dispensing system having a patient identification feature comprising the RFID system described hereinabove and methods of using the same.

In one embodiment, when the wrist worn RFID tag is removed, the RFID tag or inlay is damaged or destroyed and the drug dispensing system becomes non-functional.

In another embodiment, the dispensing device is activated and dispenses a drug dosage form following patient identification.

In yet another embodiment, the drug dispensing device system further comprises small volume drug dosage forms and a timed lock-out feature, wherein the timed lock-out feature provides for a set lock-out time, and the dispensing device cannot be activated during the set lock-out time.

The drug dispensing device system may further comprise a sufentanil-containing drug dosage form for use in the inpatient/hospital setting or in the outpatient setting.

In one further embodiment, methods for controlled access and safe administration of sufentanil to the oral mucosal membrane of a subject in the outpatient setting are provided.

In one aspect of this embodiment, a multiple single-dose dispenser (MSD) containing a plurality of single dose applicators (SDAs) is provided. Each SDA comprises a drug dosage form with an amount of sufentanil selected from the group consisting of 5 mcg, 10 mcg, 15 mcg, 20 mcg, 30 mcg, 40 mcg, 50 mcg, 60 mcg, 70 mcg, 80 mcg and 100 mcg, wherein the drug dosage forms have a volume of less than 30 microliters or a mass of less than 30 mg.

The MSD may comprise one or more of the following features: (i) a lock-out feature adapted for setting a lock-out time such that an SDA cannot be removed from the MSD during the lock-out time; (ii) a dose counting feature; (iii) a patient identification feature such as RFID; and (iv) a child resistant feature.

Each SDA may comprise: (i) two case halves that house the drug dosage form; (ii) a label designed to provide for child resistance; (iii) a pusher; and (iv) a bridge feature that breaks away as the pusher is advanced to deliver a drug dosage form to the oral mucosal membrane.

BRIEF DESCRIPTION OF THE DRAWINGS

FIG. 4 is a schematic depiction of an exemplary dispensing device showing features designed to block or retard saliva and moisture ingress.

FIGS. 6A-D are a schematic depiction of an exemplary proboscis of a drug dispensing device wherein the proboscis has an S-shape and comprises a shroud.

FIGS. 8A and 8B are photographs of exemplary multiple dose dispensers, holding a plurality of SDAs (FIG. 8A) and holding a plurality of SDAs and further showing an SDA after removal the multiple dose dispenser (FIG. 8B).

FIGS. 9A-C are schematic depictions of an exemplary multiple dose dispenser holding a plurality of SDAs.

FIGS. 10A-C are schematic depictions of another exemplary multiple dose dispenser holding a plurality of SDAs. Included is a means for sensing when each SDA is removed from the device as well as a port which can be plugged into a computer do download user dose history information.

DETAILED DESCRIPTION OF THE INVENTION

Figure 1:
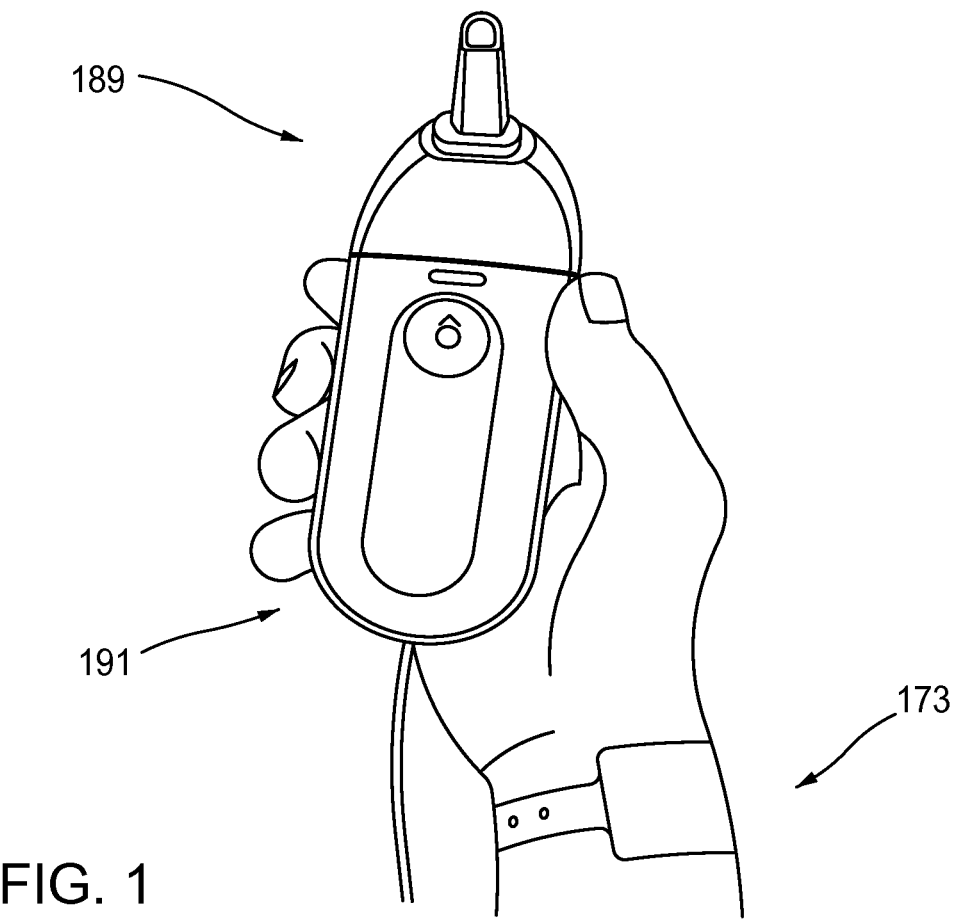
FIG. 1 is a photograph of a handheld and portable drug dispensing device and corresponding and RFID bracelet.

The following disclosure describes handheld and portable drug dispensing devices, systems and methods for their use in oral transmucosal administration of small volume drug dosage forms. A detailed disclosure of the devices, systems and methods for administration of drug dosage forms are provided hereinbelow. The present invention generally encompasses: (1) drug dosage forms (tablets); (2) drug dispensing devices; (3) systems that include a drug dispensing device and a drug dosage form; and (4) methods for using such drug dispensing devices and systems.

The disclosure is generally directed to dispensing devices for dispensing any of a number of types of small volume dosage forms to the oral mucosa, methods of using such dispensing devices and systems comprising the same. The invention is not limited to the specific devices, systems and methodology or syndromes described herein, as these may, of course, vary. It is also to be understood that the terminology used herein is for the purpose of describing particular embodiments only, and is not intended to limit the scope of the present invention.

It must be noted that as used herein and in the appended claims, the singular forms "a", "and", and "the" include plural references unless the context clearly dictates otherwise. Thus, for example, reference to "a drug formulation" includes a plurality of such formulations and reference to "a drug delivery device" includes systems comprising drug formulations and devices for containment, storage and delivery of such formulations.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

DEFINITIONS

The terms "formulation" and "drug formulation" or "drug dosage form" as used herein refer to a physical composition containing at least one therapeutic agent, which may be provided in any of a number of dosage forms for delivery to a subject. The dosage form may be provided to the patient as a lozenge, pill, capsule, membrane, strip, liquid, patch, pad, film, gum, gel, spray or other form. In one embodiment, the drug dosage form is a solid, e.g., a lozenge, a pill, a tablet, a membrane or a strip. The claimed "drug dosage forms" are also referred to herein as tablets.

The term "drug" as used herein is generally meant to refer to any substance that alters the physiology of an animal. The term "drug" may be used interchangeably herein with the terms "therapeutic agent", "medication", "pharmacologically active agent" and the like. It will be understood that a "drug" formulation may include more than one therapeutic agent, wherein exemplary combinations of therapeutic agents include a combination of two or more drugs.

The term "subject" includes any subject, generally a mammal (e.g., human, canine, feline, equine, bovine, ungulate etc.), adult or child, in which treatment for a disorder is desired. The terms "subject" and "patient" may be used interchangeably herein.

The term "transmucosal" delivery of a drug and the like is meant to encompass all forms of delivery across or through a mucous membrane. In particular, "oral transmucosal drug delivery" and "oral transmucosal administration" as used herein refer to drug delivery that occurs substantially via the oral transmucosal route and not via swallowing followed by GI absorption. This includes delivery via buccal, sublingual and gum transmucosal areas. Transmucosal dosage forms are designed to provide for a dissolution/erosion rate that allows for maximal delivery via the oral mucosa, typically via placement of the dosage form in the sublingual cavity.

As used herein, "sublingual", means literally "under the tongue" and refers to a method of administering substances via the mouth in such a way that the substances are rapidly absorbed via the blood vessels under the tongue rather than via the digestive tract. Absorption occurs via highly vascularized mucosa and allows a substance more direct access to the blood circulation, providing for direct systemic administration independent of gastro-intestinal influences.

The term "treatment" or "management" of a medical disorder or condition is used herein to generally describe regression, suppression, or mitigation of symptoms of the medical disorder or condition so as to make the subject more comfortable as determined by subjective criteria, objective criteria, or both.

"Operatively connected" as used herein means the components are provided in a device so as to function as intended to achieve an aim. For example, a memory device operatively connected to a CPU which is further operatively connected to a release mechanism may be meant to indicate that, upon actuation, the CPU communicates with the memory device to check the status or history of drug delivery, and then further communicates with the release mechanism (e.g., via a solenoid and a switch) to release and dispense a drug.

The term "FOB" refers to a small, portable handheld, powered electronic docking device that can be used in conjunction with the drug dispensing device to upload data, download data, control access to the drug dispensing device, control access to the drug dosage forms, or enhance or otherwise alter the user interface of the drug dispensing device. A FOB may communicate and dock with a drug dispensing device either in a wired or wireless fashion. A FOB may be adapted to attach to a cord so as to allow the FOB to hang from the neck of a patient, or healthcare professional such as a physician or caregiver, particularly in the hospital setting. A drug dispensing device may communicate with a physician or care giver via the FOB.

The terms "dispensing device", "drug dispensing device", "dispenser", "drug dispenser", "drug dosage dispenser" and "drug delivery device", are used interchangeably herein with the term "dispensing device" and refer to a device that dispenses a drug dosage form. A single dose applicator is considered to be a "drug dispensing device". The dispensing device provides a mechanism for controlled and safe delivery of a medication formulated in a dosage form for delivery to the oral mucosa of a patient and is adapted for storage and/or delivery of a dosage form such as a lozenge, pill, tablet, capsule, membrane, strip, liquid, patch, film, strip, gel, spray or other form.

The term "systems that include a drug dosage form and a dispensing device" as used herein refers to a drug dispensing system for delivery and/or monitoring of drug administration. A system may be used to monitor and deliver both efficacious and safe dosages such that the amount of drug delivered, and the corresponding safety and efficacy are enhanced over currently available systems. The system may have one or more features that provide for improved safety and ease of use over currently available systems including a security feature that prevents unauthorized access to the stored drugs, such as a dosing lock-out feature, a dose counting feature, a memory means for retaining information about dose delivery, and an interface for bidirectional exchange of information with a user, a drug cartridge, or another device such as a computer, as well as a means for identifying a device user such as the patient or a health care provider in order to provide for controlled drug access.

The term "proboscis" is used interchangeably with the terms "dispensing tip" and "delivery tip", and refers to a dispensing and/or positioning tip of a drug dispenser that delivers a dosage form to a desired location (e.g. the oral mucosa).

The term "shroud" is used to describe a partial or complete covering of the delivery port of the proboscis to protect the delivery port from contact with saliva or other moisture in the oral cavity.

Features of Dispensing Devices

Figure 2:
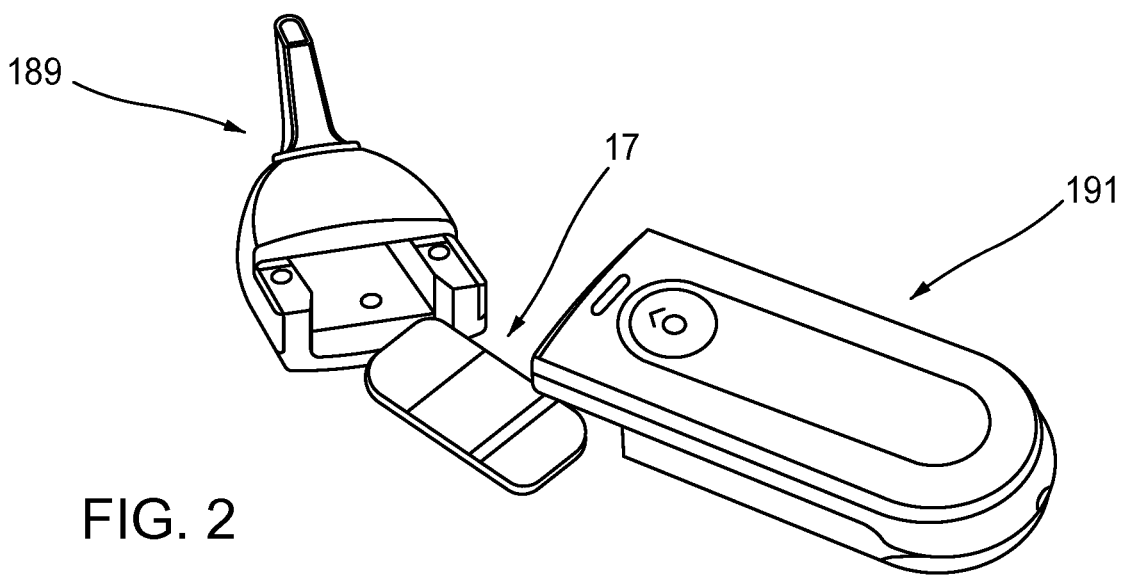
FIG. 2 is a photograph of a handheld and portable device comprised of a disposable dispensing end, a reusable controller end and a disposable drug cartridge.

One exemplary embodiment of the drug dispensing device is handheld and portable, as shown in FIG. 1. This embodiment of the drug dispensing device has a disposable dispensing end 189 and a reusable controller 191. In this embodiment, a disposable drug cartridge 17 is locked into place when the disposable dispensing end 189, and reusable controller end 191 are latched to one another (FIG. 2). In another embodiment, the device is capable of dispensing multiple drug dosage forms, a single dose at a time for delivery via the oral mucosa, e.g., into the sublingual or buccal space.

The drug dispensing device has a housing with a dispensing end which typically has a proboscis with a shroud which can block or retard saliva ingress and saliva contact with the tablet exit port, as further described herein below.

In some embodiments of the invention, the drug dispensing device is manually actuated and fully disposable, e.g., a single dose applicator (SDA).

In other embodiments, the drug dispensing device is actuated by an electromechanical means. The claimed drug dispensing devices have a number of additional features, further described below.

User Identification Feature

The claimed dispensing devices comprise a detecting means for patient identification such as: fingerprint identification; RFID detection with the use of an active or passive RFID tag on a bracelet, necklace, clip, belt, strap, ring, adhesive patch (e.g., on the finger or thumb of the patient), or an implant, or other means of locating and affixing the tag; retinal identification; DNA identification; voice recognition; password or code entry; physical key; electronic or magnetic key; personal area network identification using the human body or clothing as a data or signal conduit; optical scanner or face recognition; sonic; subsonic or ultrasonic identification; or any other means of identifying an individual and verifying their identity. The dispensing device may employ one or more means to identify the user, enabling the system to determine if a dispensing request is being made in an authorized or unauthorized manner.

It is important for effective delivery of many drugs to ensure that the dispensing device is not accidentally or intentionally used by an unauthorized individual thus preventing accidental or intentional diversion of the drug. Such user identification systems may recognize one or more users, for example, in an inpatient hospital setting the dispensing device can be programmed to recognize the patient to whom it is prescribed, and/or an authorized healthcare provider such as a nurse or physician.

One method of user identification is the use of a short distance ("near field") passive RFID tag attached to a bracelet, a necklace, an adhesive patch placed on the end of the patient's finger or thumb, a ring, a clothing tag, an orally mounted device such as an orthodontic retainer, a belt, a strap, some combination of the above, or another location. When an RFID tag is used in the "near field", roughly defined as about 16% of the wavelength of the received signal, the tag behaves in the inductive mode of operation, coupling the reader and tag antenna magnetically. The near field is characterized by at least two features: first, a rapid decline in field strength with distance, and second, a strong directionality of the signal. In the near field, the signal strength falls off very rapidly, with a signal strength loss of approximately 60 dB per decade in distance. Good inductive coupling between the transmitter antenna and the RFID tag antenna occurs when two antennas are oriented in parallel planes with the axes through the center of each antenna in close proximity. A second orientation for good inductive coupling is when the two antennas are oriented in the same plane, and in close proximity Strong signal strength (robust user identification) is provided when the device is very close to the RFID tag (as exemplified by the system shown in FIG. 1; details of a RFID bracelet embodiment shown in FIG. 3A and details of an RFID antenna embodiment shown in FIG. 3B). At the same time, a very poor signal is provided when the device is further away or misaligned from the tag, which helps prevent unauthorized use by someone other than the patient who attempts to use the device. It is preferable to operate in this near field region with good antenna alignment. Furthermore, it is preferable to operate with a very short distance of adequate signal strength for a positive identification, so that it is very difficult to receive a signal if the device is not in the proper orientation and proximity to the RFID tag. To attain a short distance and a proper alignment between antennas, the dispensing device may be designed so as to properly locate the RFID reader antenna, mounted in the dispensing device, adjacent an RFID tag antenna, mounted, for example, on a wrist band or bracelet, a finger or thumb ring, or a clothing tag on the collar, or an adhesive patch on the hand, arm, cheek, neck, or elsewhere. Furthermore, an RFID tag antenna on a wrist band or bracelet may be held in proper alignment and location by means of a small adhesive patch that prevents the bracelet from moving or rotating on the wrist.

RFID technology is widely utilized for inventory, logistical tracking, and other supply chain and related functions. A passive RFID tag includes a chip and an antenna and when exposed to, and energized by, radio-frequency energy from the RFID reader, the tag transmits its identification which is captured by the reader. A tag may have either read functionality or read/write functionality. An active RFID tag operates in the same manner as a passive RFID tag, except it has its own power source, such as a battery.

Figure 3A:
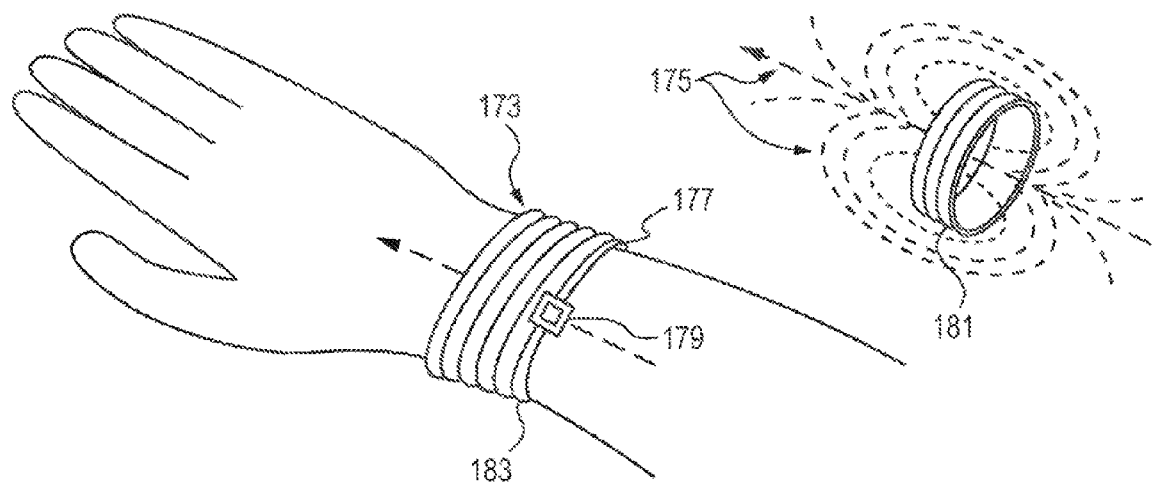
FIGS. 3A and 3B are schematic depictions of an exemplary RFID bracelet and an annular antenna.

An RFID tag, inlay or label comprises an RFID die or chip component (comprising an electronic identification circuit and a coupling means), a circuit and an antenna structure coupled to the coupling means. This tag component can be embedded into a bracelet, necklace, ring, adhesive patch, clothing tag, orally mounted device, belt, strap, or combination there of—any of which may be worn by the patient. An exemplary wrist worn RFID tag, or bracelet, is shown in FIG. 1 and a detailed embodiment is shown in FIG. 3A. In FIG. 3A, the conductor is wrapped one or more times around the wrist such that the antenna axis is effectively parallel to the axis of the wrist and forearm. This configuration allows for a wrist worn RFID tag such as a bracelet to have a directional orientation aligned toward a device in the palm of one's hand as shown in FIG. 3A. The fixed orientation allows coupling with the RFID reader housed within a handheld device. FIG. 3A shows an RFID circuit board 179, a coiled conductor antenna 177, an annular antenna on the RFID bracelet 183, where the annular antenna produces an electromagnetic field directed towards one's hand 181. Providing this directionality is not possible with existing RFID bracelet technology.

The claimed RFID tag, inlay or label comprises a die or chip, a circuit and antenna that includes one or more wraps of a conductor 187 that circumvent the wrist to form a bracelet 173 as shown in FIGS. 1 and 3A.

There is a continuing, unfilled need for devices, methods, and systems comprising a wrist worn RFID tag which can couple or communicate with a handheld device permitting patient identification by the handheld device. The present invention addresses this need.

In one example of this embodiment, the dispensing device employs a high frequency RFID reader for use in the inpatient (hospital, clinic, etc.) setting, operating on or near the 13.56 MHz frequency band, and the patient is fitted with a disposable version of the aforementioned RFID bracelet with annular antenna designed in such a way that if the bracelet or wrist band is removed, the RFID tag, its antenna, or another component of the associated circuit is damaged or destroyed, rendering the bracelet or wrist band non-functional. In one example, the range of the RFID communication is short, between 0 inches and 12 inches preferably, more preferably between 0 and 8 inches, and most preferably between 0 and 6 inches.

In one preferred embodiment, the RFID signal is directional and symmetrical, allowing proper use by the intended patient to be transparent, usable by right or left hands equally, easy and reliable, while at the same time making unauthorized use by another individual difficult.

Figure 3B:
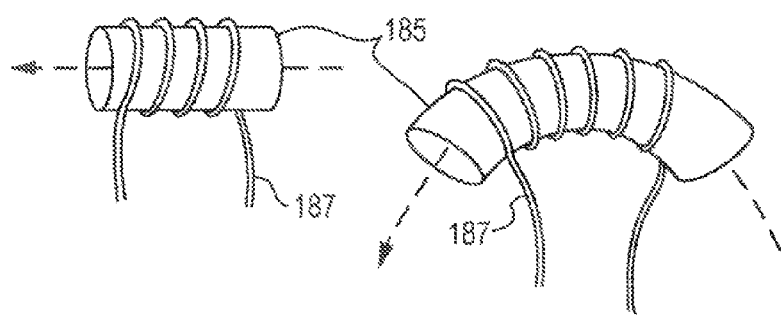

In another embodiment, the RFID reader antenna employs a ferrite 185 to direct or focus the field toward the RFID tag, as shown in FIG. 3B. The ferrite antenna is bidirectional but not symmetrical, having a coiled conductor 187, e.g., made of ferrite 185, such that the RFID tag is designed to work equally well when the RFID reader device is held in either the left or right hand (FIG. 3B). Additionally, this ferrite antenna provides for increased range and increased directionality.

Finger or Thumb Patch RFID Tag

In yet another embodiment, the RFID tag is provided as a patch or sticker, which is designed to be attached (adhered) to the end of a finger or the thumb of a patient. The patch or sticker may be attached to any area around the finger or hand, including the pad side or the nail side of the fingers/thumb. The patch typically comprises a microchip attached to an antenna which is packaged in a way that it adheres to the end of a finger or the thumb of a patient for the period of time that a given dispensing device is used by the patient. The tag picks up signals from and sends signals to a reader contained within a drug dispensing device. The tag contains unique information, specific to the reader located in the dispensing device it is paired with. The reader has one or more antennas, which emit radio waves and receive signals back from the tag. When the finger or thumb patch is held sufficiently close to the drug dispensing device, the reader receives a signal which enables the dispensing device to dispense a dosage form, so long as the device is not in a timed lock-out period.

Lock Out

In one embodiment, the dispensing device has a timed lock-out feature which provides for a set lock out time at regular intervals or time periods.

The timed lock-out period for the claimed dispensing device is typically from 5 minutes to 60 minutes, from 10 minutes to 40 minutes, from 15 minutes to 30 minutes, typically 15 or 20 minutes. The timed lock-out period may be set at any one minute interval from 5 to 60 minutes, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes. The lock-out time is typically preset, however, the dispensing device may provide a means for adjusting the lock-out time.

There can also be a second tier lockout, for example a scenario where the patient is permitted to take a tablet once every 20 minutes, not to exceed 12 doses in a 24 hour period.

Blocking/Retarding Saliva and Moisture Ingress

In some embodiments, the device comprises a means for minimizing or eliminating saliva ingress and moisture ingress onto and into the device: (1) to avoid wetting the dosage forms therein, whether in the dispensing track or in the primary dosage package (cartridge); (2) to isolate any saliva that enters the dispensing device in such a manner that the dosage forms therein remain dry; (3) to absorb or adsorb any saliva that enters the dispensing device in such a manner that the dosage forms remain dry; (4) to block saliva and moisture from entering the device, to protect the dosage forms from vapor and liquid phase moisture; (5) to block incidental contact of the tongue or mucosa on the tablet exit port or proboscis that can lead to wetting and ultimately the adherence of the tablet to the device, or (6) any combination thereof.

The device may also comprise a means for preventing and/or controlling humidity ingress into and within the device due to ambient conditions outside the device. The dispensing device may rely on valves, pads, seals, the rest position of push rod, proboscis design and a shroud to minimize or eliminate saliva ingress or moisture into the dispensing device during administration of the dosage forms.

The means for minimizing or eliminating saliva ingress or preventing other moisture from entering the dispensing device includes, but is not limited to, one or more flexible or rigid seals, valves, one or more flexible or rigid wipers, use of one or more absorbent material components such as a desiccant or pad, a door or latch that is manually or automatically opened and closed, multiple stage delivery systems, a positive air pressure and airflow, or an air gap or prescribed distance or barrier/shroud maintained between the tablet delivery orifice and the mucus membrane tissues within the mouth that may transport the saliva. The shroud limits the ability of the tongue or oral mucosa to contact the dosage form dispensing area, thereby controlling saliva contact and ingress. By inhibiting or eliminating the "wetness" inside the shroud and on the surface of the valve/seal, the dosage form is dispensed without adhesion occurring between the dosage form and the shroud or valve/seal. In this embodiment, the drug dispensing device provides a means for minimizing or eliminating saliva ingress into the device during administration of the drug to the oral mucosa of the patient.

Means for trapping or otherwise isolating saliva or moisture once it has entered the device include, but are not limited to, a hydrophilic wicking material or component, an absorbent or adsorbent material or component, a desiccant material or component, a separate track or channel for moisture to collect, a separate channel to communicate moisture to the absorbents or adsorbents, or any combination of these materials or components, and are described in detail in U.S. Patent Publication Nos. 20070186923, 20080164275, 20080268023 and PCT Publication Nos. WO 2007/081947, WO2008/085763 and WO2008/085764, each of which is expressly incorporated by reference herein.

To protect the drug dosage forms from exposure to moisture either from humidity, saliva ingress, or accidental exposure to other water based liquids, the dispensing device and the container or cartridge which houses the dosage form within the device may or may not contain a desiccant. In some embodiments, the design of the dispensing device, in particular, the proboscis and shroud are sufficient to minimize or eliminate saliva ingress and moisture ingress into the device. In such cases, there is no desiccant material in the dispensing device. In one embodiment, the desiccant may snap into a cavity in the side of the cartridge. There are holes in the desiccant cavity that connect it to the tablet stack, exposing the tablets to desiccant and keeping them dry.

The proboscis design for use in the device is characterized by a distal device shape, typically an S-shape, that aids in use of the device and/or placement of the tip on the oral mucosa of the subject. The shape typically has curves, angles, and geometries such that it enables proper use of the device and placement of the dosage form on the oral mucosa of the subject, e.g., in the sublingual space. The shroud of the device has a geometry that forms a barrier between the device and the oral mucosa and tongue, a relief for dosage form delivery, and an interior that is hydrophobic or hydrophilic and serves to minimize or eliminate saliva ingress or moisture ingress by creating a barrier from the oral mucosa contacting the valve area and dosage form, aiding in dosage form dispensing and discouraging dosage form adherence to the shroud. The shroud may have a rounded interior surface or other geometries to mitigate the dosage form adhering to the shroud. The shroud may also include another component to aid in keeping the interior hydrophobic or hydrophilic by absorbing or adsorbing saliva and moisture in order to inhibit the dosage form from sticking to the surface. The shroud limits the ability of the tongue or oral mucosa to contact the dosage form dispensing area, thereby controlling saliva contact and ingress as well as the wetting of the device tablet exit port.

FIG. 4 is a schematic depiction of an exemplary dispensing device wherein the dispensing tip comprises a shroud 29 having a one or more of: a wiping or sealing valve 33 or 35, an absorbent pad 39, a drug drying chamber/moisture communication channel 43, desiccant in the channel 45, a cartridge 17 containing dosage forms 67 and desiccant in the cartridge 47.

Figure 5A:
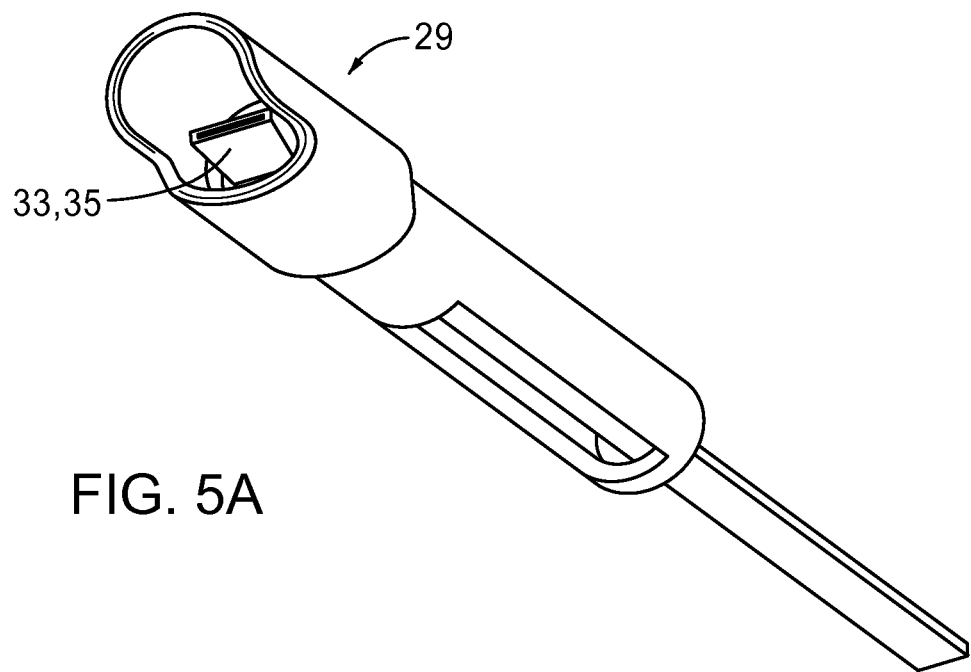
FIGS. 5A and B are schematic depictions of an exemplary geometry for a dispensing tip of a drug dispensing device.
Figure 5B:
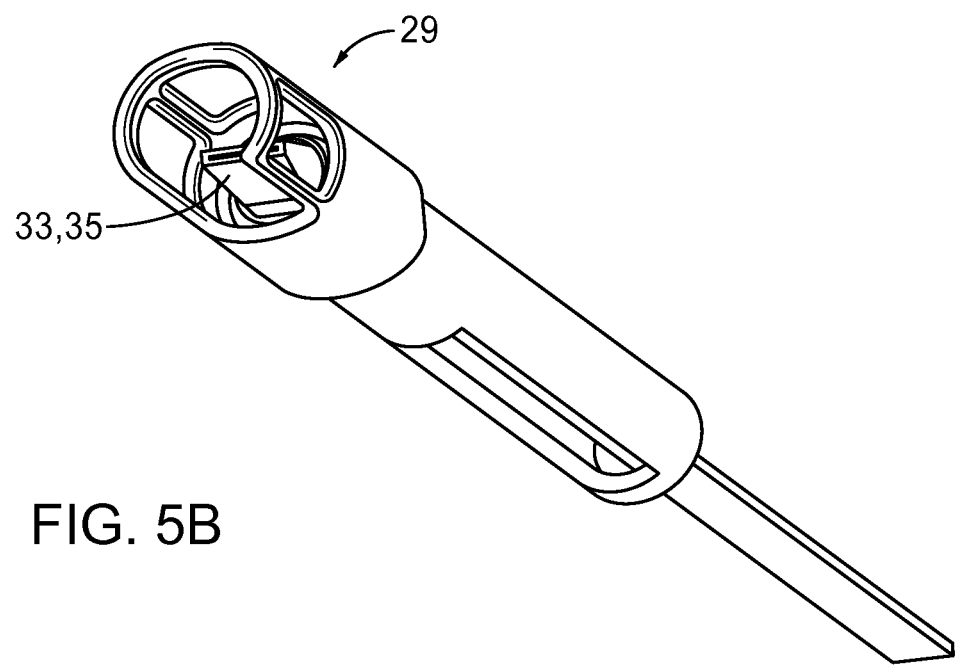
Figure 6A:
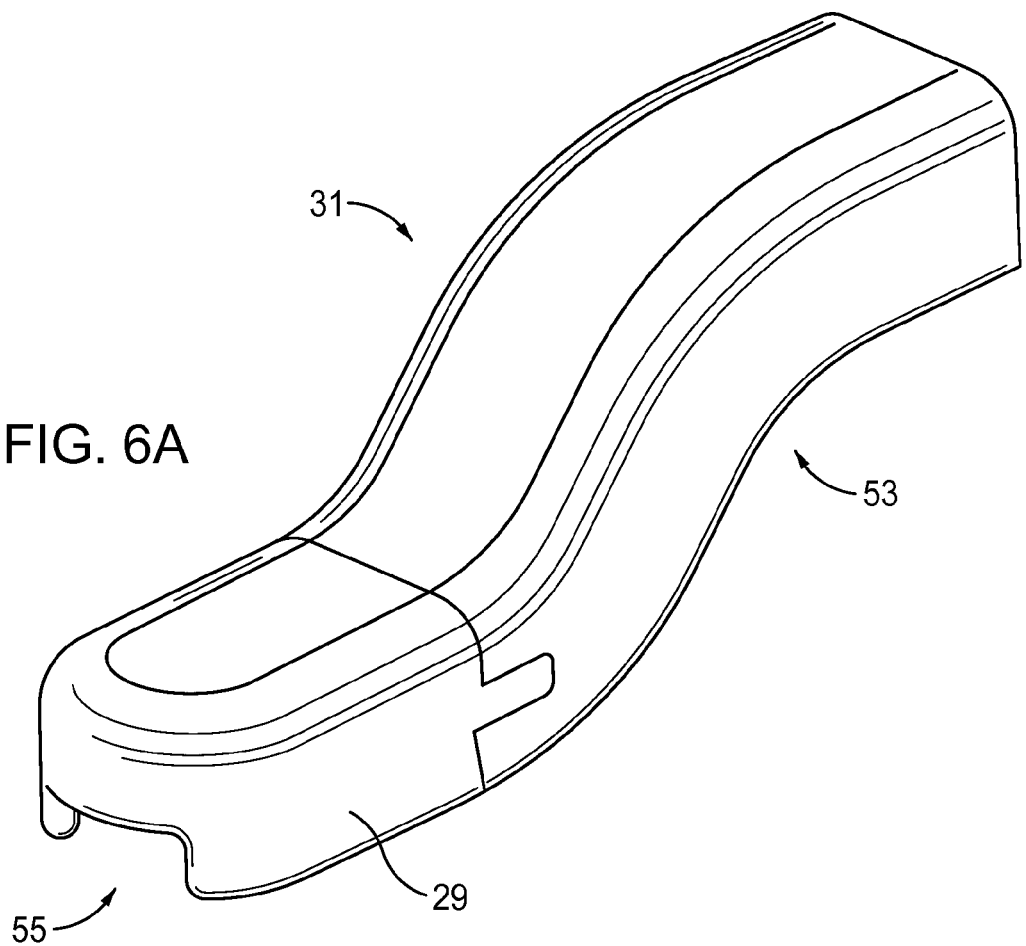
Figure 6B:
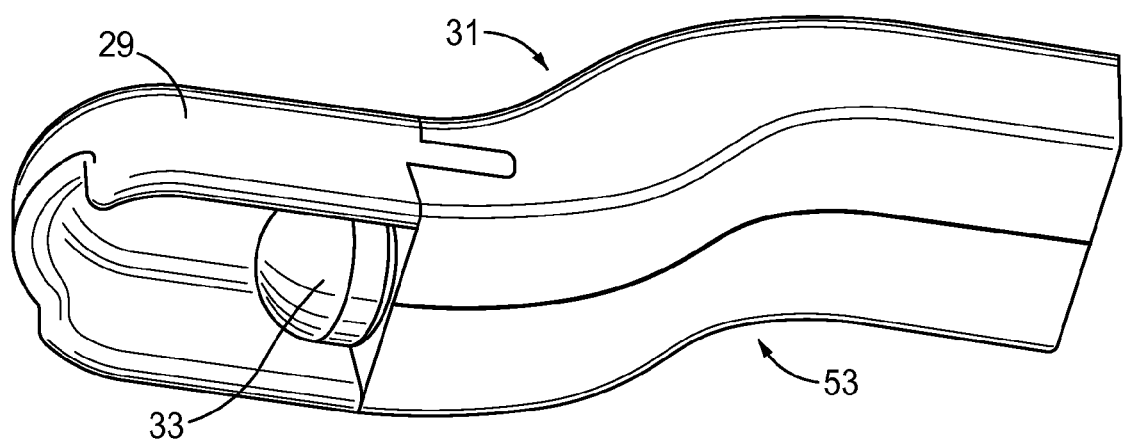

FIGS. 5A and B are schematic depictions of an exemplary geometry for a dispensing tip that prevents contact of one or more seals 33, 35 with the moist or wet surface of the oral mucosa via a shroud 29.

FIGS. 6A-D are a schematic depiction of an exemplary proboscis 31 of the dispensing device wherein the proboscis 31 has an S-shape 53 and comprises a shroud 29, a valve 33 for dispensing a dosage form 67 and a cut-out/relief 55 for the dosage form to be placed against the oral mucosa and not moved when the device is withdrawn following dispensing. The shroud shields the valve from moisture and saliva ingress from the tongue and other mucosa and provides an area for the dosage form to exit the device without "sticking" to the wetted distal valve or shroud area. The valve functions with the shroud to control saliva and moisture ingress, as well as aid in delivery of the dosage form.

The claimed drug dispensing may be used to administer a tablet that is sensitive to moisture and/or humidity. In some cases, the dispensing device includes a tablet cartridge 17 (e.g., as shown in FIG. 2) that protects the tablet from liquid and vapor phase moisture, including humidity, liquid moisture, saliva, mucus, etc. The cartridge may be cylindrical, disk-shaped, helical, rectilinear, non-ordered, or may take the form of any assemblage of tablets that allows the drug dispensing device to dispense them in a controlled manner. To prevent the unused tablets from absorbing moisture or otherwise becoming exposed to moisture prior to use, the cartridge may provide a means of sealing the tablets from exposure to moisture. In some embodiments, all of the tablets in a cartridge may be packaged together in a foil sealed compartment.

In the case of medications, such as sufentanil, that are sensitive to oxygen when provided as a solid tablet, the primary package (e.g., a cartridge), may contain the solid sufentanil tablet and an oxygen scavenger, as a means to minimize or eliminate generation of oxidative degradation products upon storage, as detailed in U.S. patent application Ser. No. 12/275,485, expressly incorporated by reference herein.

The pushrod design of the dispensing device is described in U.S. Patent Publication Nos. 20070186923 and 20080164275, also expressly incorporated by reference herein.

Dosing History/Feedback

Further embodiments of the device include the ability to store historical use information and the ability to transmit such information. The device may be capable of unidirectional (downloading) or bidirectional information transfer. For example, such an exchange of information may be accomplished by downloading stored information to a computer through a physically wired interface, such as a USB or other communication connection. Alternatively, information may be communicated via a wireless system, e.g. Bluetooth, Wifi, or other RF technology.

In another embodiment, the dispensing device has a dose counting feature that monitors and stores the history of drug usage. Such information may include historical use information, for example the number of dosages stored and dispensed, the state of the dispenser, and the times of dispensing.

Device Setup

The claimed dispensing device may be capable of self-calibration of the dispense mechanism, or the device may be calibrated manually. This process may employ a "shipping tablet" as the first tablet dispensed from the device. This shipping tablet has a feature or features that differentiate it from a drug-containing tablet and the push rod. The differentiating feature may be physical, optical, RF, electronic or magnetic. This features can be recognized by the device during setup to ensure that the device is working correctly without requiring the dispensing of a drug-containing tablet. This approach also confirms, during setup, that a 'new cartridge' is being used.

Additional Features

The claimed dispensing device may also provide the ability to recognize a specific cartridge by a mechanical, optical (e.g. bar code), electronic (e.g. microchip), magnetic, radio frequency, chemical, or other means of detecting and identifying the cartridge. In one exemplary embodiment of the invention, the cartridge contains a physical keying detail on the cartridge that is physically detected by a sensor or switch or a series of sensors or switches in the dispensing device. Furthermore, the dispensing device may communicate uni-directionally or bi-directionally with the cartridge to exchange information. Such information may include drug name, dosage strength, usage information, lockout period, manufacturing lot number, indications for use, side effects, drug interactions, date of manufacture, date of expiration, serial number, number of doses in the cartridge, or any other relevant information. The dispensing device may be able to write, in addition to read, information to the cartridge, like date used, health care provider or patient identification, number of doses remaining, etc.

The claimed dispensing device provides mechanical protection for the dosage forms contained therein, preventing breakage, chipping, hydration etc., thereby allowing for dispensing of the undamaged dosage forms contained therein. This is of particular importance for small fragile and friable dosage forms.

The drug dispensing device may be powered by a battery, capacitor, fuel cell, external electrical power supply, or other power supply source, or may require no electrical power, but be manually activated.

In some embodiments, the dispensing device is capable of issuing alarms or other notifications when functional or safety issues arise. The alarm or other notification may trigger an alert on the dispensing device, on a dock or other peripheral device; on a computer or by means of a wired or wireless network, or may alert other remote devices. The alarm or notification may be audible, tactile, visual, or may employ other means of notifying one or more individuals.

Base Station/Docking Station

In some embodiments the drug dispensing system includes a base station for recharging one or more drug dispensing devices and a portable docking FOB between uses. In addition to recharging the drug dispensing devices and FOBs, the base station may provide one or more of the following functionality: wireless or wired connectivity to a peripheral device, computer or network; feedback on the charging state for the devices being recharges; an interface for viewing, adding, deleting, or modifying the data on a drug dispensing device or FOB; a means for synchronizing data between multiple drug dispensing devices and/or FOBs; a means for updating a drug dispensing device; and a means for conducting a diagnostic test on drug dispensing devices and/or FOBs.

A drug dispensing device may communicate with a physician or care giver, via a base station, dock or a wired or wireless communication means.

The dispensing device may employ one or more levels of interface for different types of authorized users, for example the patient, the nurse, the physician, pharmacist or other authorized medical or healthcare personnel. These different interfaces may include components such as keypads, buttons, graphical icons and instructions, lights, LED's, monochrome or color graphical or text displays, touch-screens, LCD's, sounds, tactile feedback, voice recognition interfaces, and other input and output devices and means. The activity, or mode, of the user interface may be determined by the mode of operation of the dispensing device, by a login or access activity by a user such as a password or code entry, by the connection or disconnection of the dispensing device from a dock, computer, or network, or by the detection of an authorized access key, such as a key, and/or RFID tag, combination, password, barcode, or similar technology. Upon changing the interface mode, the functionality of the device may be changed, either activating, inactivating or changing the functionality of the various interface components described above. By allowing the device to have one or more interface modes, with differing functionality associated with each one, the device can be optimized for various uses.

Single Dose Applicators (SDAs) and Multiple Dose Dispensers (MDDs)

The invention further provides dispensing devices and methods of using the same for oral transmucosal delivery of a drug dosage form using a single dose applicator (SDA). Use of the SDA is not limited to any particular type of device or patient population. As such, the claimed SDAs find utility in drug delivery to pediatric, adult and non-human mammalian subjects.

In one embodiment, a SDA is used to administer a variety of drug dosage forms, including a solid tablet, a liquid capsule, a gel capsule, a liquid, a gel, a powder, a film, a strip, a ribbon, a spray, a mist, a patch, or any other suitable drug dosage form.

The SDA may be provided as a pair of forceps, a syringe, a stick or rod, a straw, a pad, a capsule, a cup, a spoon, a strip, a tube, an applicator, a dropper, a patch, an adhesive pad, an adhesive film, a sprayer, an atomizer, or any other form suitable for the application of a single drug dosage form to the oral mucosa of a subject, e.g., the oral mucosa in the sublingual space. As will be understood by one of skill in the art, the SDA design may vary, so long as it is effective to place a drug dosage form, such as a tablet, in the desired location on an oral mucosal membrane, e.g., in the sublingual space, in a manner that preserves integrity of the drug dosage form in the dispensing process. After use, the SDA is disposed of, so as to eliminate the risk of contaminating the drug dispensing device with saliva, or other contaminants.

The SDA may contain the dosage form within, may have the drug dosage form attached or affixed to it, may have the dosage form dissolved in it, and may afford a seal against moisture, humidity, and light. The SDA may be manually manipulated by a patient, healthcare provider, or other user to place the dosage form in the proper location for drug delivery. The SDA may also be child resistant and/or enable abuse deterrence.

The single-dose applicator is used to deliver tablets or other dosage forms into the hand, the mouth, under the tongue, or to other locations appropriate for specific drug delivery needs.

In one preferred embodiment, a single-dose applicator or drug dispensing device is used to deliver a dosage form directly to the oral mucosa, e.g., the sublingual space.

The dosage form inside the SDA remains dry prior to dispensing, at which point a single dosage form is dispensed onto the oral mucosa, and the patient's saliva wets the tablet and allows for tablet disintegration/erosion and drug dissolution. After use, the SDA is disposed of.

Figures 7A, 7B:
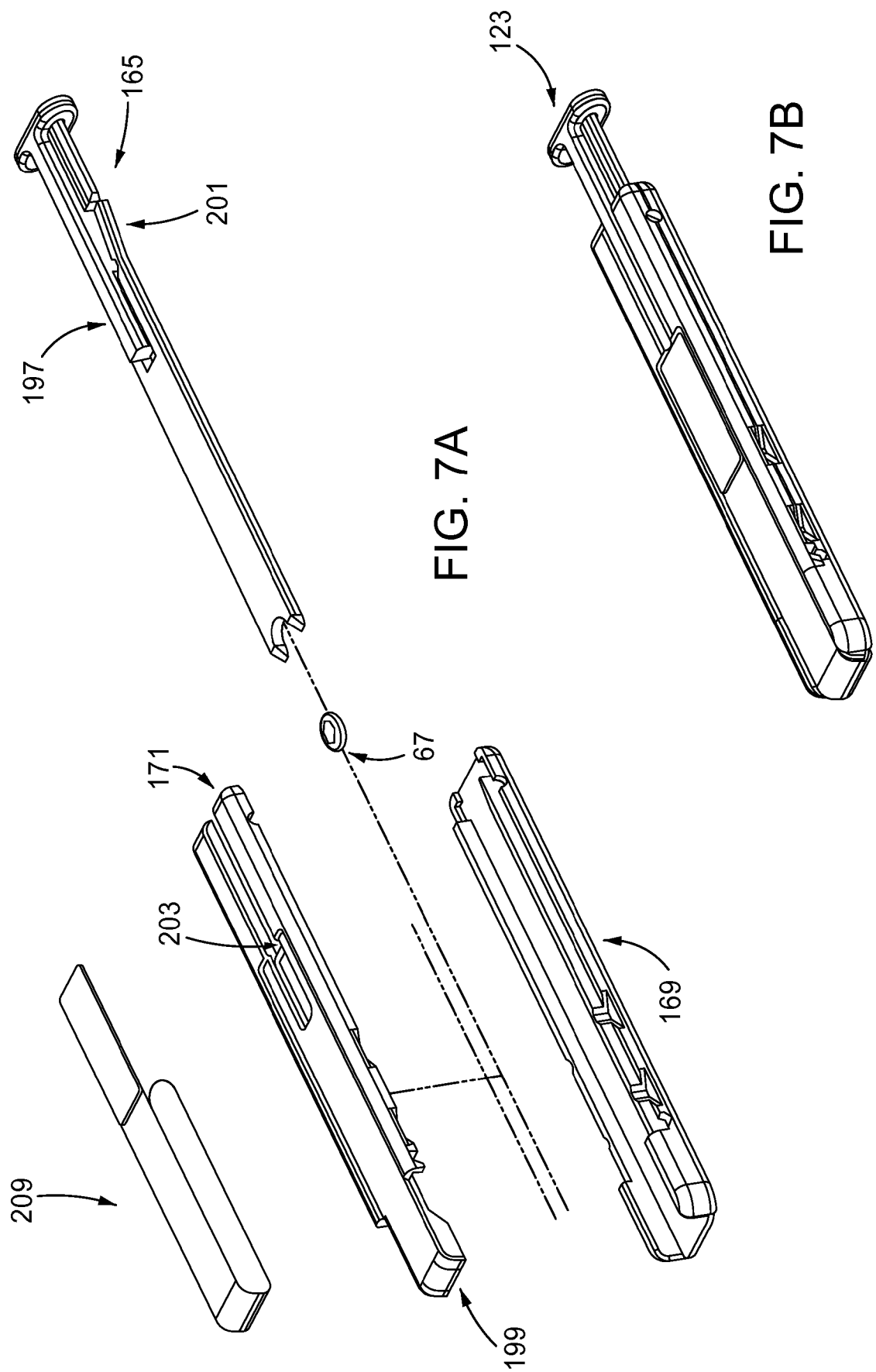
FIGS. 7A-B are schematic depictions of an exemplary single dose applicator (SDA).

In one approach, for sublingual administration, a small volume dosage form is administered by placement under the tongue, adjacent to the frenulum with a syringe, a syringe-type SDA, a stick or rod, a straw, a dropper, or any other form suitable for the application of a single drug dosage form, including but not limited to a SDA. Numerous examples of SDAs are described in U.S. patent application Ser. No. 12/187,937 and PCT Publication No. W02008/085765, each of which is expressly incorporated by reference herein. FIGS. 7A and B provide detailed drawings of an exemplary SDA; FIG. 7A is an exploded view and FIG. 7B is an assembled view. The embodiment of the device shown in FIGS. 7A and B consists of two case halves, 171 and 169, a pusher 165, and a label, 209. For assembly, the two case halves are snapped together and the label 209 is applied so that the tip 199 is not allowed to deflect while the label 209 is still in place, providing one level of child resistant packaging. The tablet 67 is placed in the cavity between the case halves 171 and 169, and the pusher 165 is snapped into place trapping the tablet inside of the assembly. In this configuration as shown in FIG. 7A, the snap feature on the pusher 201 keeps the pusher 165 from coming out of the assembly and the raised portion on the pusher 197 bares against the edge of the label 209 to keep the pusher from advancing the tablet 67 out of the tip 199 thus acting as an additional level of child resistant packaging. During use, the user first removes the label 209 from the assembly. In this configuration, while the label 209 is no longer present to resist advancement of the pusher 165, there is a small bridge feature 203 in one or both of the case halves to provide some resistance so that accidental pusher actuation does not occur. To dispense the tablet 67, a user places the tip of the SDA 199 sublingually and pushes on the back of the pusher 165 hard enough to overcome the strength of the bridge feature 203. At this time, the bridge feature 203 breaks away and the pusher advances flexing the tip of the SDA 199 open while advancing the tablet out of the device and into the sublingual space.

In one embodiment, the claimed drug dispensing device contains a plurality of SDAs, provided in a cartridge or individually packaged which is designed to dispense a single SDA containing a single drug dosage form for use by the patient, healthcare provider, or user. The drug dispensing device may dispense single SDAs and comprise any of a number of the features described herein which are advantageous to safe and effective dispensing of single drug dosage forms.

A plurality of SDAs may be provided as a series of individual SDAs attached by a backing or housed in a multiple dose dispenser 137 or multiple dose storage unit. In some cases, SDAs 123 are stored in a multiple dose storage unit which may be referred to as a multiple single-dose dispenser (MSD) or multiple dose dispenser (MDD) 137. Exemplary MSDs or MDDs are shown in FIGS. 8A-B, 9A-C, 10A-C, and in U.S. patent application Ser. No. 12/187,937 and PCT Publication No. W02008/085765, each of which is expressly incorporated by reference herein. In each embodiment for use in dispensing SDAs, the MSD or MDD may comprise a sensing means 205 for detecting when an SDA is removed from the device along with electronics capable of recording and storing information as to when the SDA is removed. The MSD or MDD 137 is designed to be child resistant. FIGS. 8A-B, 9A-C and 10A-C show a plurality of SDAs 123 in various exemplary MSD or MDD configurations 137. As shown in FIGS. 9A and 9B, the MSD/MDD may comprise a port 207, which when plugged into a computer allows for the download of stored information. See e.g., FIGS. 8A-B, 9A-C and 10A-C, which illustrate exemplary multiple dose applicators 137 for delivering dispensing drug dosage forms, each individually packaged in a SDA 123.

Dosage Forms

The dispensing devices and SDAs described herein provide for single or repeated dispensing of individual (single) small volume drug dosage forms for oral transmucosal administration to a patient.

The term "small volume drug dosage form" or "small volume dosage form" is used herein with reference to a small volume dosage form or tablet that has a volume of less than 100 mcl and a mass of less than 100 mg, a volume of less than 30 mcl and a mass of less than 30 mg, or a volume of from about 3 mcl to about 15 mcl or a mass of from about 3 mg to about 15 mg. More specifically, the dosage form has a mass of less than 100 mg, 90 mg, 80 mg, 70 mg, 60 mg, 50 mg, 40 mg, 30 mg, 29 mg, 28 mg, 27 mg, 26 mg, 25 mg, 24 mg, 23 mg, 22 mg, 21 mg, 20 mg, 19 mg, 18 mg, 17 mg, 16 mg, 15 mg, 14 mg, 13 mg, 12 mg, 11 mg, 10 mg, 9 mg, 8 mg, 7 mg, 6 mg or 5 mg or a volume of less than 100 mcl, 90 mcl, 80 mcl, 70 mcl, 60 mcl, 50 mcl, 40 mcl, 30 mcl, 29 mcl, 28 mcl, 27 mcl, 26 mcl, 25 mcl, 24 mcl, 23 mcl, 22 mcl, 21 mcl, 20 mcl, 19 mcl, 18 mcl, 17 mcl, 16 mcl, 15 mcl, 14 mcl, 13 mcl, 12 mcl, 11 mcl, 10 mcl, 9 mcl, 8 mcl, 7 mcl, 6 mcl or 5 mcl.

In one embodiment, when subjected to an in vitro dissolution test in a Type II USP dissolution apparatus, about 75%, 80%, 85%, 90%, 95% or more of the total amount of sufentanil in the tablet is released within 8 or 10 minutes. In another embodiment, when subjected to an in vitro dissolution test in a Type II USP dissolution apparatus, about 75%, 80%, 85%, 90%, 95% or more of the total amount of sufentanil in the tablet is released within 12 minutes.

The "dosage forms" may be administered with a drug dispensing device or SDA, typically have bioadhesive characteristics and may form a hydrogel upon contact with an aqueous solution. The "small volume drug dosage form" or "small volume dosage form may be referred to as a "Nano-Tab™".

A dosage form delivered using the drug dispensing devices and SDAs described herein finds utility in oral transmucosal administration of any drug that can be absorbed via the transmucosal route and can benefit from this route of administration, for example if the drug is susceptible to GI or first-pass metabolism.

In one aspect, the device or SDA contains a dosage form comprising from about 1mcg to 10 mg of a drug, from about 2 mcg to about 1 mg, from about 5 mcg to about 200 mcg of a drug or from about 10 mcg to about 100 mcg of a drug. Typically the drug will be used for the treatment of pain.

In another aspect, the dosage from comprises an opioid selected from the group consisting of sufentanil, alfentanil, fentanyl, lofentanil, carfentanil, remifentanil, trefentanil, and mirfentanil.

In one exemplary embodiment, the claimed oral transmucosal drug dosage form contains from about 0.25 mcg to about 200 mcg of sufentanil, from about 5 mcg to 150 mcg of sufentanil, from about 10 mcg to 100 mcg of sufentanil, or from about 10 mcg to about 30 mcg of sufentanil. A single SDA may include dosage forms comprising different amounts of sufentanil. Sufentanil may be provided as sufentanil citrate, sufentanil base, or a combination thereof.

Solid Sufentanil Dosage Forms

In general, small volume solid dosage forms containing from about 2 mcg to about 200 mcg of sufentanil may be used for oral transmucosal drug delivery. The dosage forms contain sufentanil, alone or in combination with another drug, e.g., a benzodiazepine such as triazolam.

The process for manufacture of solid dosage forms, e.g., tablets, pills, capsules, strips, films, powders, lozenges, membranes, patches, film or other forms, comprising sufentanil, typically involves the use of an aqueous and/or organic solvent.

The dosage forms comprise a formulation that is neither effervescent nor does it comprise an essentially water-free, ordered mixture of microparticles of drug adhered to the surface of carrier particles, where the carrier particles are substantially larger than the microparticles of drug.

Typical formulations for preparation of sufentanil-containing solid dosage forms and methods of making them are described in U.S. Patent Publication Nos. 20070207207 and 20080166404, expressly incorporated by reference herein. An exemplary formulation for use in making a sufentanil-containing solid dosage form is bioadhesive and comprises from about 0.04% to about 4% sufentanil, from about 0.08% to about 1.7% sufentanil or from abut 0.1% to about 2.0% sufentanil, e.g., about 0.04%, 0.08%, 0.1%, 0.2%, 2.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.2%, 1.3%, 1.4%, 1.5%, 1.6%, 1.7%, 1.8%, 1.9%, 2.0%, 2.2%, 2.2%, 2.4%, 2.5%, 2.6%, 2.8%, 3.0%, 3.2%, 3.5% or 4% sufentanil.

Numerous suitable nontoxic pharmaceutically acceptable carriers for use in sufentanil-containing solid dosage forms can be found in Remington's Pharmaceutical Sciences, 17th Edition, 1985.

Systems for Administration of Dosage Forms to a Patient

In one exemplary embodiment, the present invention provides a system, comprising: (1) a dispensing device or SDA for administration of a drug dosage form to the oral mucosa of a subject, for example, a small-volume dosage form or NanoTab™; (2) a dosage form for oral transmucosal administration, such as a small-volume dosage form or NanoTab™; and (3) a subject.

In another exemplary embodiment, the system for administration of dosage forms to a patient using the claimed drug dispensing device further includes a drug dispensing device wherein the dispensing device comprises a means for patient identification and/or a lock-out feature.

Additional features which may be included in the system includes a docking station or other docking means, a means of communication with a computer network such as a bidirectional communication link with a local or remote computer system (wired or wireless), a pharmaceutical network monitoring and control apparatus, a computer network that stores, records and transits information about drug delivery from the device and one or more user interfaces.

Utility

Exemplary conditions treatable with the claimed dispensing devices and SDAs, include but are not limited to acute pain, post operative pain, cancer breakthrough pain, procedural pain and anxiety, nausea and/or vomiting.

One use for the claimed drug dispensing device arises in the inpatient setting. For example, the need for rapid treatment of acute pain occurs in many different clinical situations, including pain following an accident; post-operative pain; rheumatoid arthritis; back injury; cancer; etc. in the hospital setting. Post-operatively, for example, patients suffer from severe pain for the first few days followed by days of mild to moderate levels of pain.

In one embodiment of the invention, a cartridge for use in the device in the inpatient or outpatient setting may hold sufficient drug dosage forms for a single day or multiple 1-5 days of treatment, e.g., 40 tablets useful for up to 48 hours of treatment.

In another embodiment the drug dispensing device is comprised of a disposable drug cartridge, a disposable dispensing end, a reusable controller end, a user identification means like an RFID tag, a portable docking FOB for controlling and accessing the drug dispensing device, and a base station for recharging the reusable dispensing end and the portable docking FOB. In this embodiment the drug cartridge is loaded into the disposable dispensing end, which, in turn, is connected to the reusable controller end and affixed together. This assembly completes the drug dispensing device which is capable of dispensing dosage forms to the patient upon request, providing a lockout period between dosing, recording dosing and usage history, and allowing this history and the drug dispensing device settings to be reviewed or electronically downloaded. An RFID tag would be affixed to a patient so as to provide a wireless identification means that would enable the drug dispensing device to operate properly when in proximity to the correct RFID tag. A healthcare provider could use the portable docking FOB to dock with the drug dispensing device, allowing access to settings, controls, history, and other features. When not in use, the reusable controller end and the portable docking FOB could be placed in the base station to recharge the batteries or power supply.

In yet another embodiment, the drug dispensing device comprises a disposable drug cartridge containing 40 tablets and useful for up to 48 hours of treatment, a disposable dispensing end, a reusable controller end, a user identification means like a directional RFID tag, a lockout feature (e.g., with a set lockout time of 20 minutes) and a base station for recharging the reusable dispensing end. In this embodiment, the controller contains a user interface that can be used to upload data from the device, download data such as dosing history or the number of tablets remaining in the cartridge, control access to the drug dispensing device, control access to the drug dosage forms, control access to a tether or other connectable apparatus, and communicate bidirectionally with a hospital computer system or other computer network by means of a wired or wireless connection. In this embodiment, the drug cartridge is loaded into the disposable dispensing end, which, in turn, is connected to the reusable controller end and affixed together and the dispensing end and cartridge are disposable. When outside the lockout window, the drug dispensing device is capable of dispensing dosage forms to a patient upon request when the patient pushes a "dispense button". The dispensing device can record dosing and usage information, and is capable of allowing the information and the drug dispensing device settings to be reviewed or electronically downloaded. In one approach, a directional RFID tag is affixed to the patient so as to provide a wireless identification means that would enable the drug dispensing device to operate properly when in proximity to the correct RFID tag. In other approaches, a different patient identification means such as fingerprint matching is employed. In either case, a healthcare provider interacts directly with the controller end to adjust settings, controls, download usage information, etc. When not in use, the reusable controller end is placed in the base station to recharge the batteries.

When used in the inpatient setting, the claimed dispensing device offers several features and advantages over the state of the art in patient drug administration. The dispensing device allows healthcare providers to provide drug dosage forms to a patient for self administration of PRN ("Pro Re Nata") medications. PRN refers to drugs that are taken as needed, such as for pain, nausea, constipation, anxiety, etc. The claimed drug dispensing device may be used to dispense any PRN medication in any drug dosage form in the inpatient setting affording any combination of the features set forth above, as described in U.S. Patent Publication No. 20070299687.

In another embodiment, a MSD comprising thirty (30) SDAs is prescribed for a patient who is subjected to an outpatient surgical procedure at a clinic. The patient self administers the first drug dosage form with the assistance of a caregiver while at the clinic, then takes the MSD home for self administration of one or more doses of the drug.

The claimed dispensing device may also be used in the outpatient setting or in both the inpatient and outpatient setting, e.g., for treatment of post operative pain or cancer breakthrough pain. Further examples of outpatient indications where the claimed dispensing device finds utility include pain associated with physical trauma, chronic pain, chronic breakthrough pain, anxiety, insomnia, hypertension, coronary artery disease, depression, psychosis, addiction, ADHD, high blood pressure, diabetes, constipation, nausea, vertigo and others. See, e.g., U.S. Patent Publication No. 20070260491

To effectively assist in the dispensing of drugs in the acute outpatient setting, the dispensing device may provide some or all of the following features: allow the patient to self administer the medication; record dosing history; allow the dosing history to be read or transferred to a computer, network or other electronic device; deter tampering or diversion; have child safety; have lockout; deliver the drug dosage form to the appropriate location (e.g. sublingual, or buccal); record a dosing administration or a temperature or humidity event.

When used in the outpatient acute setting (home, office, field, etc.), the dispensing device offers several features and advantages over the state of the art in outpatient drug administration. The dispensing device allows individuals to self administer drugs in accordance with physician, healthcare provider, or drug label guidelines. The drug dispensing devices, SDAs, methods and systems described herein find utility in this setting. A patient may transition from the inpatient environment where a drug dosage form is delivered using the dispensing device (e.g., as shown in FIGS. 1-2 and 4-6) to the outpatient setting where the same drug dosage form is administered using an SDA/MSD (e.g., as shown as in FIGS. 7-10). This allows a patient to move from the inpatient to the outpatient setting without having to switch medications.

All publications mentioned herein are incorporated herein by reference in their entirety for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

Although the foregoing has been described in some detail by way of illustration and example for purposes of clarity and understanding, it will be apparent to those skilled in the art that certain changes and modifications may be practiced. Various aspects of the invention have been achieved by a series of experiments, some of which are described by way of the following non-limiting examples. Therefore, the description and examples should not be construed as limiting the scope of the invention, which is delineated by the appended description of exemplary embodiments.

The invention claimed is:

1. An apparatus, comprising:
   a housing defining an actuation pathway and a channel in communication with the actuation pathway;
   a delivery member, at least a portion of the delivery member being disposed within the actuation pathway such that a distal end portion of the delivery member and a distal end portion of the housing define a volume configured to contain a drug-containing tablet, the delivery member configured to move relative to the housing in a distal direction to expel the drug-containing tablet from the volume, the delivery member including a protrusion configured to engage a portion of the housing to limit movement of the delivery member relative to the housing in a proximal direction, the delivery member including an elongate protrusion slidably disposed within the channel, an edge of the elongate protrusion configured to limit movement of the delivery member relative to the housing in the distal direction; and
   a safety member removably coupled the housing, the safety member configured to limit movement of the delivery member relative to the housing in the distal direction.

2. The apparatus of claim 1, wherein the safety member is a label coupled to the distal end portion of the housing.

3. The apparatus of claim 1, wherein
   the elongate protrusion is configured to contact an edge of the safety member to limit movement of the delivery member relative to the housing in the distal direction.

4. The apparatus of claim 1, wherein the distal end portion of the housing is configured to deform when the delivery member is moved in the distal direction relative to the housing to produce an opening through which the drug-containing tablet can be expelled.

5. The apparatus of claim 1, wherein:
   the distal end portion of the housing is configured to deform when the delivery member is moved in the distal direction relative to the housing to produce an opening through which the drug-containing tablet can be expelled; and
   the safety member is configured to inhibit deformation of the distal end portion of the housing.

6. The apparatus of claim 1, wherein:
   the housing includes a bridge configured to engage the delivery member, at least a portion of the bridge configured to be separated from the housing when the delivery member is moved relative to the housing in the distal direction.

7. The apparatus of claim 1, further comprising:
   a drug-containing tablet disposed in the volume, the drug-containing tablet including a dosage of sufentanil.

8. The apparatus of claim 7, wherein the drug-containing tablet includes an amount of sufentanil selected from the group consisting of 5 mcg, 10 mcg, 15 mcg, 20 mcg, 30 mcg, 40 mcg, 50 mcg, 60 mcg, 70 mcg, 80 mcg and 100 mcg, and wherein said drug-containing tablet has a volume of less than 30 microliters or a mass less than 30 mg.

9. The apparatus of claim 1, wherein the housing and delivery member are configured to enable a user to deliver a drug-containing tablet to a sub-lingual mucosal membrane.

10. The apparatus of claim 1, wherein:
    the distal end portion of the delivery member includes a geometric surface configured to engage the distal end portion of the housing when the delivery member is moved in the distal direction relative to the housing to deform the distal end portion of the housing to produce an opening through which the drug-containing tablet can be expelled.

11. An apparatus, comprising:
a housing defining an actuation pathway;
a delivery member, at least a portion of the delivery member being disposed within the actuation pathway such that a distal end portion of the delivery member and a distal end portion of the housing define a volume configured to contain a drug-containing tablet, the delivery member configured to move relative to the housing in a distal direction to expel the drug-containing tablet from the volume, the distal end portion of the housing is configured to deform when the delivery member is moved in the distal direction to produce an opening through which the drug-containing tablet can be expelled; and
a safety member removably coupled to the distal end portion of the housing, a first portion of the safety member configured to limit deformation of the distal end portion of the housing, a second portion of the safety member configured to contact a portion of the delivery member to limit movement of the delivery member relative to the housing in the distal direction.

12. The apparatus of claim 11, wherein the safety member is a label, the first portion of the label is disposed about the distal end portion of the housing.

13. The apparatus of claim 11, wherein:
the delivery member includes a protrusion, the portion of the delivery member being disposed within the actuation pathway such that the protrusion limits movement of the delivery member relative to the housing in the distal direction.

14. The apparatus of claim 11, wherein,
the housing defines a channel in communication with the actuation pathway; and
the delivery member includes a protrusion slidably disposed within the channel, the protrusion configured to limit movement of the delivery member relative to the housing in the distal direction.

15. The apparatus of claim 11, wherein:
the housing includes a bridge member configured to engage the delivery member, the bridge member configured to resist movement of the delivery member relative to the housing in the distal direction, the bridge member configured to deform when a force applied by the delivery member in the distal direction exceeds a predetermined threshold.

16. The apparatus of claim 11, wherein the delivery member includes a protrusion configured to engage a portion of the housing to limit movement of the delivery member relative to the housing in a proximal direction.

17. The apparatus of claim 11, further comprising:
a drug-containing tablet disposed in the volume, the drug-containing tablet including a dosage of sufentanil.

18. An apparatus, comprising:
a housing defining an actuation pathway, a proximal end portion of the housing including a bridge member;
a delivery member, at least a portion of the delivery member being disposed within the actuation pathway such that a distal end portion of the delivery member and a distal end portion of the housing define a volume configured to contain a drug-containing tablet, the delivery member configured to move relative to the housing in a distal direction to expel the drug-containing tablet from the volume through an opening defined by the distal end portion of the housing, the delivery member including a first protrusion configured to engage a portion of the housing to limit movement of the delivery member relative to the housing in a proximal direction, the delivery member configured to engage the bridge member such that the bridge member deforms when a force applied by the delivery member in the distal direction exceeds a predetermined threshold; and
a safety member removably coupled to the housing, the safety member configured to limit movement of the delivery member relative to the housing in the distal direction.

19. The apparatus of claim 18, wherein the distal end portion of the housing is configured to deform when the delivery member is moved in the distal direction to expand the opening.

20. The apparatus of claim 18, wherein:
the distal end portion of the delivery member includes a geometric surface configured to engage the distal end portion of the housing when the delivery member is moved in the distal direction relative to the housing to deform the distal end portion of the housing to produce the opening.

21. The apparatus of claim 18, wherein:
the distal end portion of the housing is configured to deform when the delivery member is moved in the distal direction to expand the opening; and
a portion of the safety member is configured to limit deformation of the distal end portion of the housing.

22. The apparatus of claim 18, further comprising:
a container configured to at least partially contain the housing, the container including a sensor configured to detect when the housing is removed from the container.

23. The apparatus of claim 22, wherein:
the housing is a first housing from a plurality of housings, the container is configured to contain the plurality of housings.

24. The apparatus of claim 22, wherein the container includes:
a memory configured to store data associated with the removal of the housing; and
a port configured to operatively couple the memory to a computer.

* * * * *